United States Patent
Faulkner et al.

(10) Patent No.: US 8,454,533 B2
(45) Date of Patent: Jun. 4, 2013

(54) LANCING DEVICES AND METHODS

(75) Inventors: Allan James Faulkner, Avoch (GB); Nicholas Foley, Edinburgh (GB); David Colin Crosland, Edinburgh (GB); Matthew James Young, Edinburgh (GB); Paul Trickett, Hamilton (GB)

(73) Assignee: LifeScan Scotland Limited, Inverness (GB)

( * ) Notice: Subject to any disclaimer, the term of this patent is extended or adjusted under 35 U.S.C. 154(b) by 444 days.

(21) Appl. No.: 12/435,991

(22) Filed: May 5, 2009

(65) Prior Publication Data
US 2009/0281459 A1 Nov. 12, 2009

Related U.S. Application Data

(60) Provisional application No. 61/052,088, filed on May 9, 2008.

(51) Int. Cl.
*A61B 5/00* (2006.01)

(52) U.S. Cl.
USPC .......................................................... 600/583

(58) Field of Classification Search
USPC .......................................... 600/583; 606/182
See application file for complete search history.

(56) References Cited

U.S. PATENT DOCUMENTS

| | | |
|---|---|---|
| 4,462,405 A | 7/1984 | Ehrlich |
| 4,469,110 A | 9/1984 | Slama |
| 4,895,147 A | 1/1990 | Bodicky et al. |
| 4,976,724 A | 12/1990 | Nieto et al. |
| 5,207,699 A | 5/1993 | Coe |
| 5,324,303 A | 6/1994 | Strong et al. |
| 5,350,392 A | 9/1994 | Purcell et al. |
| 5,423,847 A | 6/1995 | Strong et al. |
| 5,628,764 A | 5/1997 | Schraga et al. |
| 5,868,772 A | 2/1999 | LeVaughn et al. |
| 5,964,718 A * | 10/1999 | Duchon et al. ................ 600/583 |
| 6,197,040 B1 | 3/2001 | LeVaughn et al. |
| 6,558,402 B1 | 5/2003 | Chelak et al. |
| 6,723,111 B2 | 4/2004 | Abulhaj et al. |
| 6,840,912 B2 | 1/2005 | Kloepfer et al. |
| 6,852,119 B1 * | 2/2005 | Abulhaj et al. ............... 606/182 |
| 6,929,650 B2 | 8/2005 | Fukuzawa et al. |

(Continued)

FOREIGN PATENT DOCUMENTS

| | | |
|---|---|---|
| EP | 1652474 A | 5/2006 |
| JP | 5-95937 A | 4/1993 |

(Continued)

OTHER PUBLICATIONS

European Extended Search Report, Munich, Germany, Sep. 8, 2012, European Application No. 12167994.8.

*Primary Examiner* — Max Hindenburg

(57) ABSTRACT

Described and illustrated herein is an exemplary lancing device. The exemplary lancing device comprises: a first housing having spaced apart proximal and distal ends disposed along a longitudinal axis; a chassis disposed in the first housing in a fixed relationship with the first housing; a movable member disposed in the chassis and configured for movement along the longitudinal axis and in the first housing; a lancet coupled to the movable member; and a lancet depth adjustment member retained by both the first and chassis so that the lancet depth adjustment member is rotatable relative to both housings to provide for a plurality of stop surfaces to the movable member. Other embodiments and methods are also described.

21 Claims, 22 Drawing Sheets

U.S. PATENT DOCUMENTS

| | | | |
|---|---|---|---|
| 7,025,774 B2 | 4/2006 | Freeman et al. | |
| 7,153,318 B2 | 12/2006 | Marshall et al. | |
| 7,713,280 B2 * | 5/2010 | Marshall et al. | 606/181 |
| 2001/0039387 A1 * | 11/2001 | Rutynowski et al. | 600/573 |
| 2003/0050655 A1 * | 3/2003 | Roe | 606/182 |
| 2003/0187470 A1 | 10/2003 | Chelak et al. | |
| 2004/0267229 A1 | 12/2004 | Moerman et al. | |
| 2005/0125017 A1 | 6/2005 | Kudrna et al. | |
| 2005/0125019 A1 | 6/2005 | Kudrna et al. | |
| 2005/0234492 A1 | 10/2005 | Tsai et al. | |
| 2006/0052809 A1 | 3/2006 | Karbowniczek et al. | |
| 2006/0100656 A1 | 5/2006 | Olson et al. | |
| 2006/0247671 A1 | 11/2006 | LeVaughn | |
| 2007/0055297 A1 | 3/2007 | Fukuzawa et al. | |
| 2007/0083222 A1 | 4/2007 | Schraga | |
| 2007/0173875 A1 | 7/2007 | Uschold | |
| 2007/0173876 A1 | 7/2007 | Aylett et al. | |
| 2007/0255300 A1 | 11/2007 | Vanhiel et al. | |
| 2008/0039885 A1 | 2/2008 | Purcell | |
| 2008/0039886 A1 | 2/2008 | Shi | |

FOREIGN PATENT DOCUMENTS

| | | |
|---|---|---|
| JP | 2005-253781 A | 9/2005 |
| WO | WO 2006/116441 A1 | 11/2006 |
| WO | WO 2006/132504 A1 | 12/2006 |
| WO | WO 2007/006399 A1 | 1/2007 |
| WO | WO 2007/130830 A | 11/2007 |

* cited by examiner

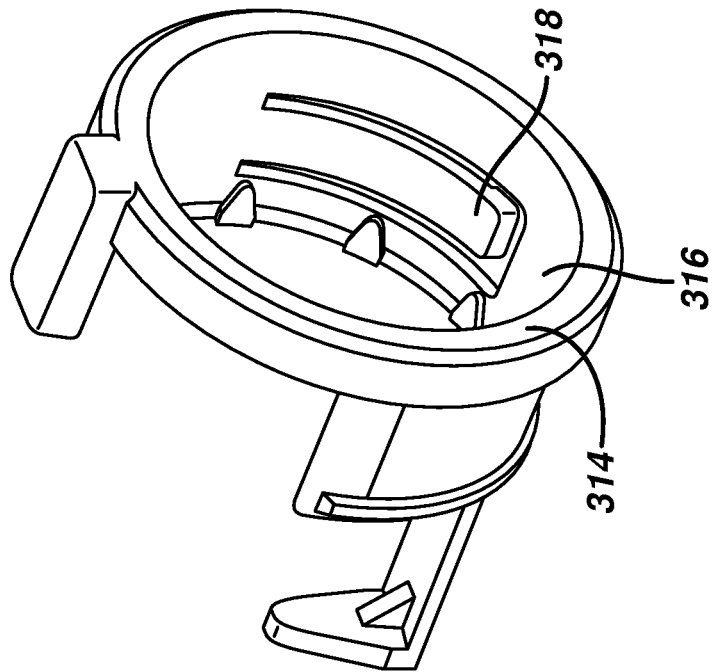
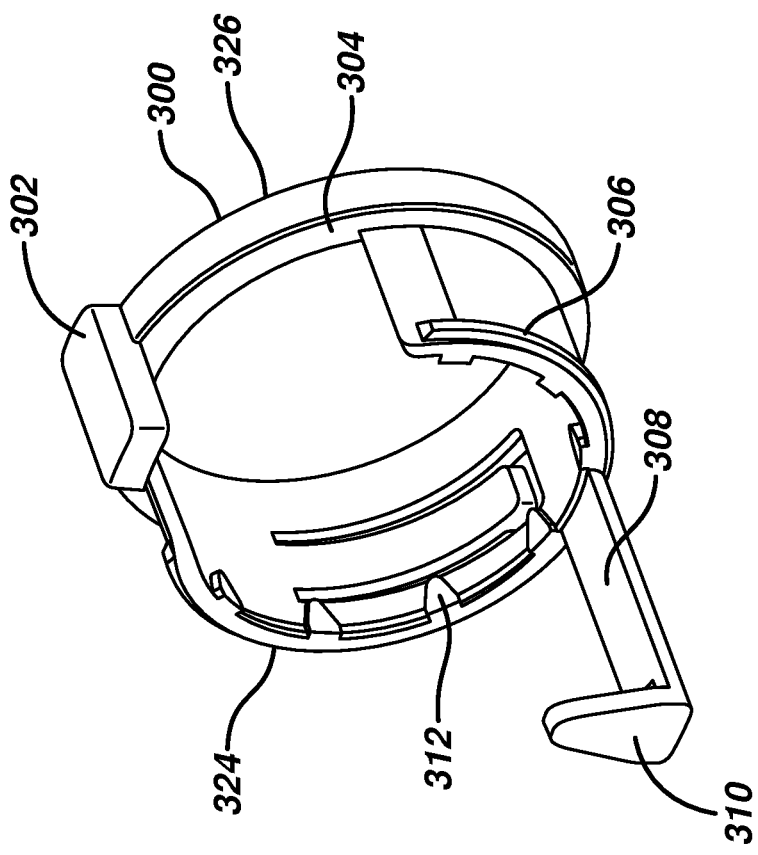

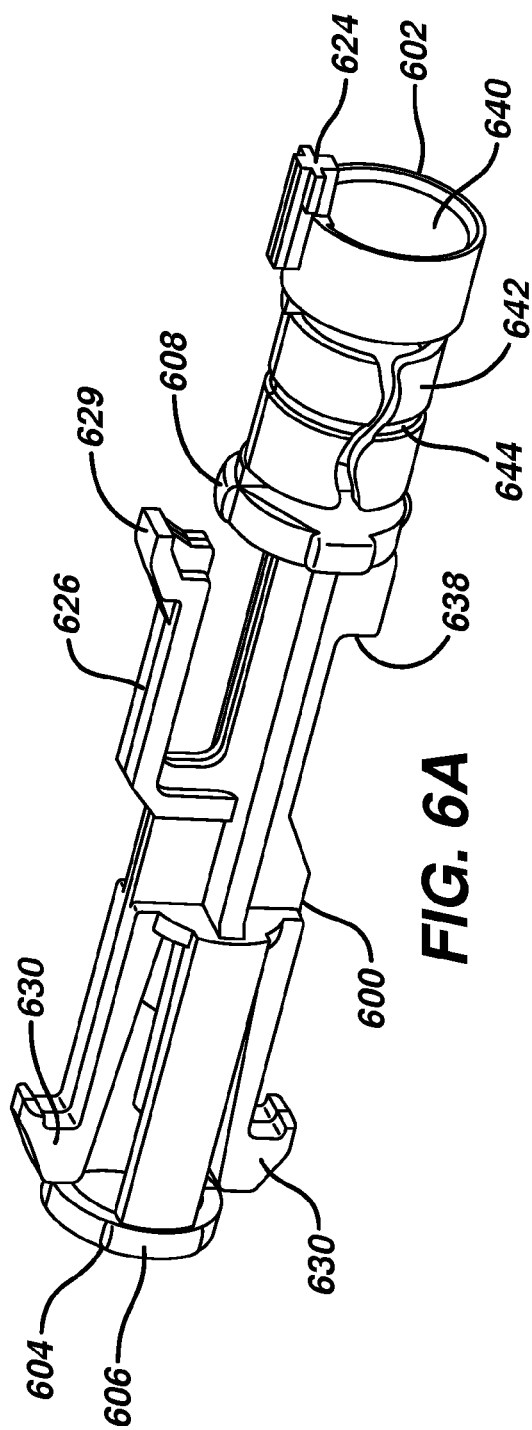
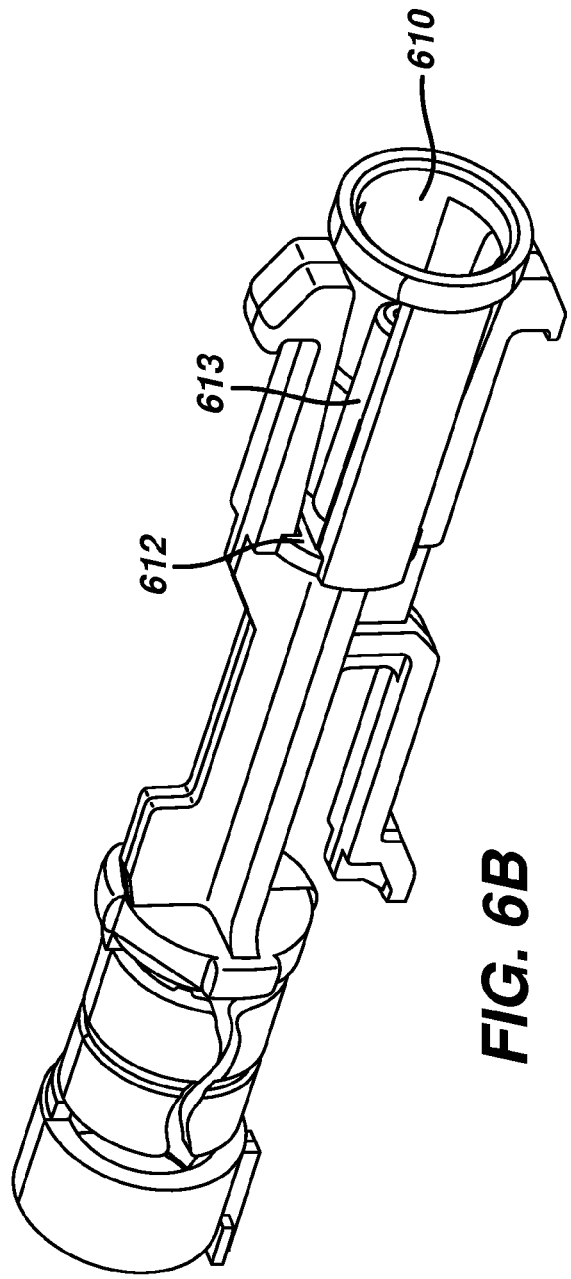

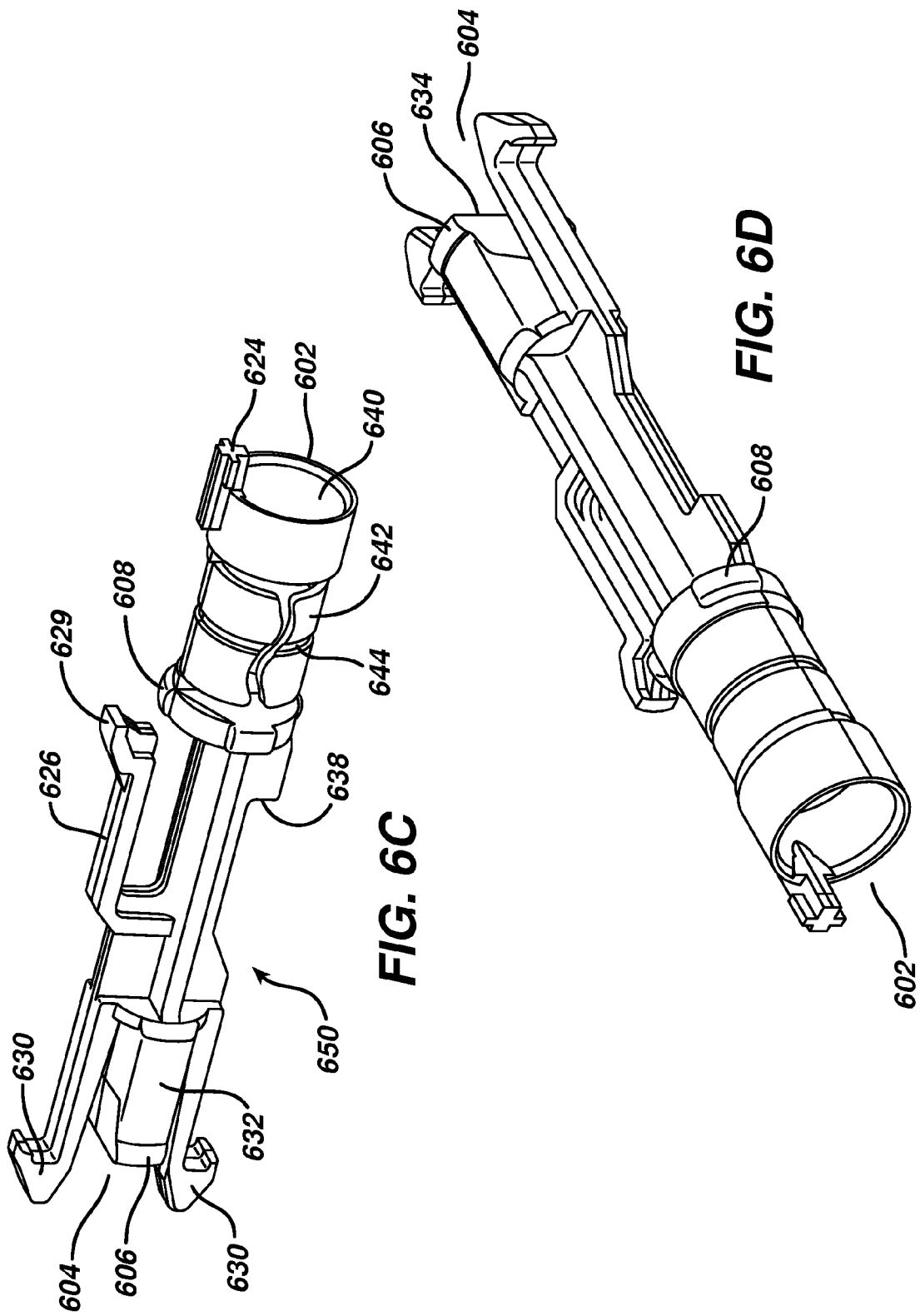

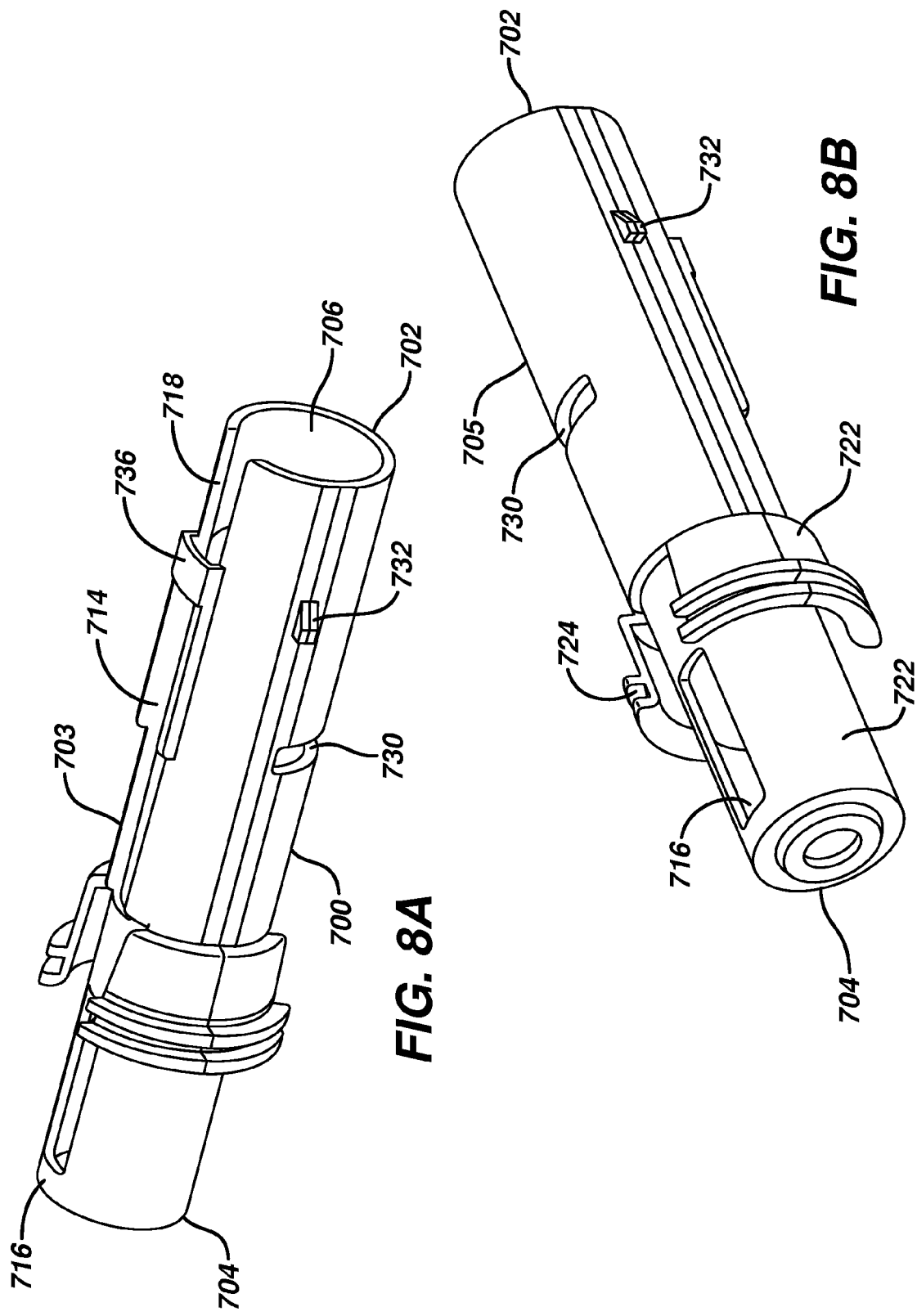

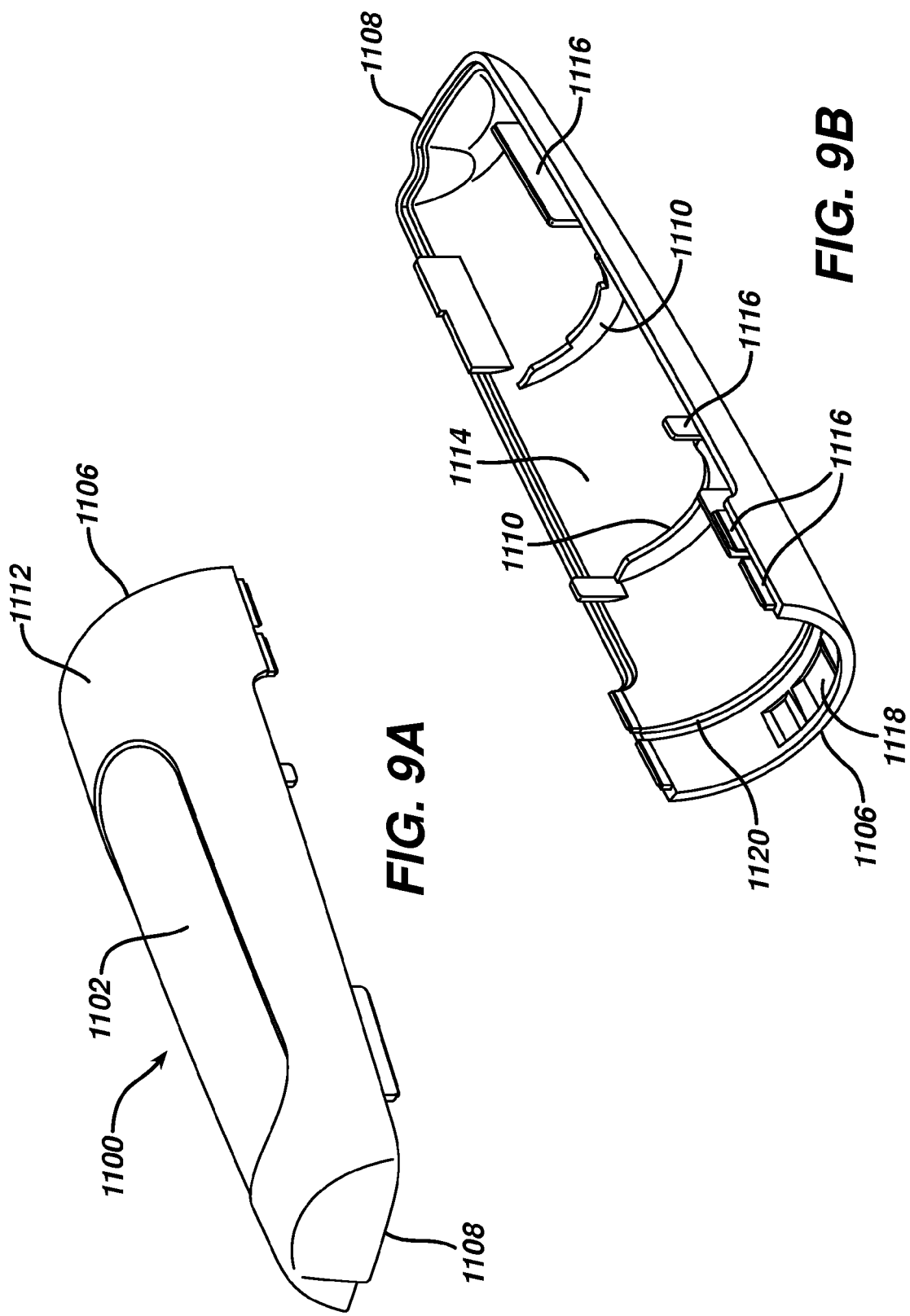

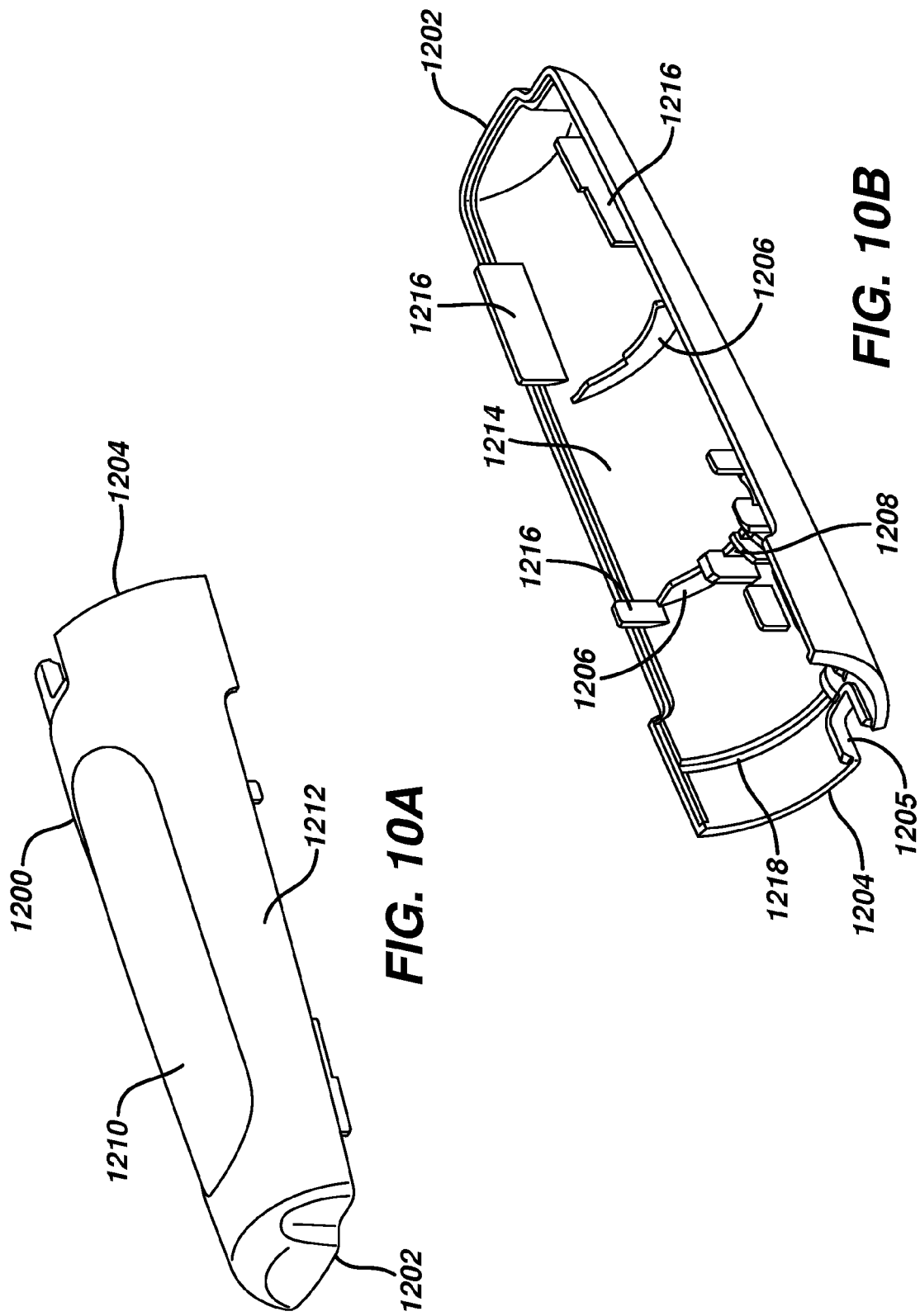

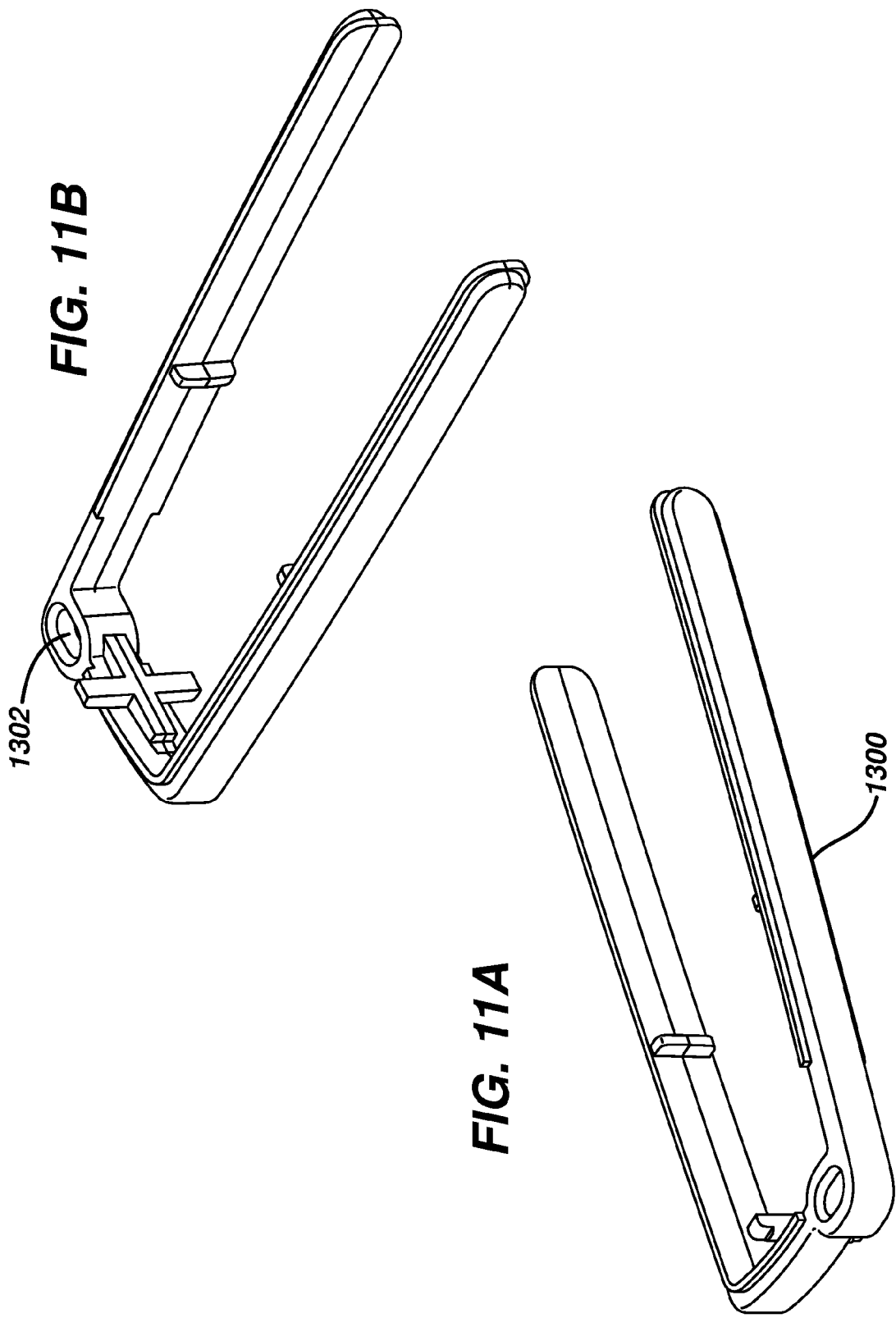

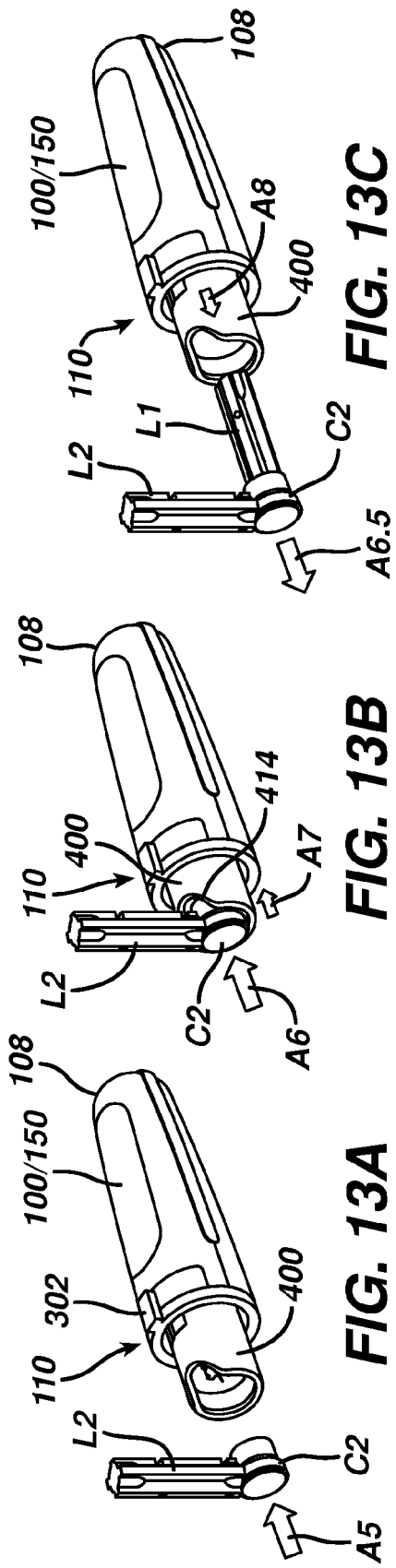
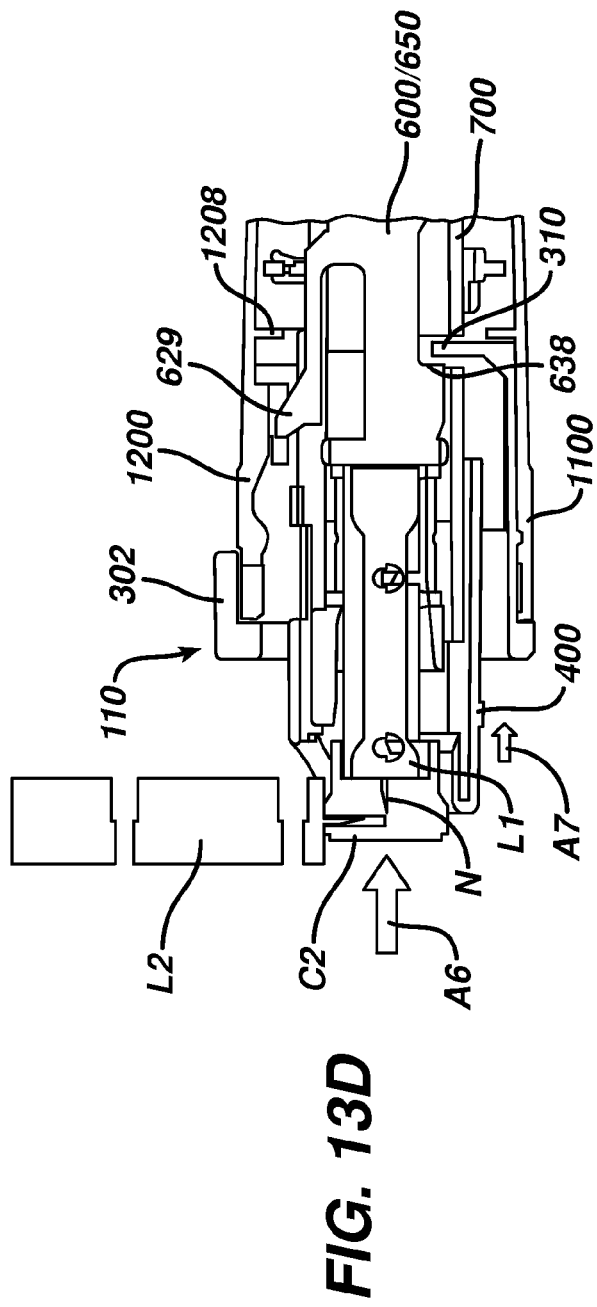
FIG. 13A  FIG. 13B  FIG. 13C  FIG. 13D

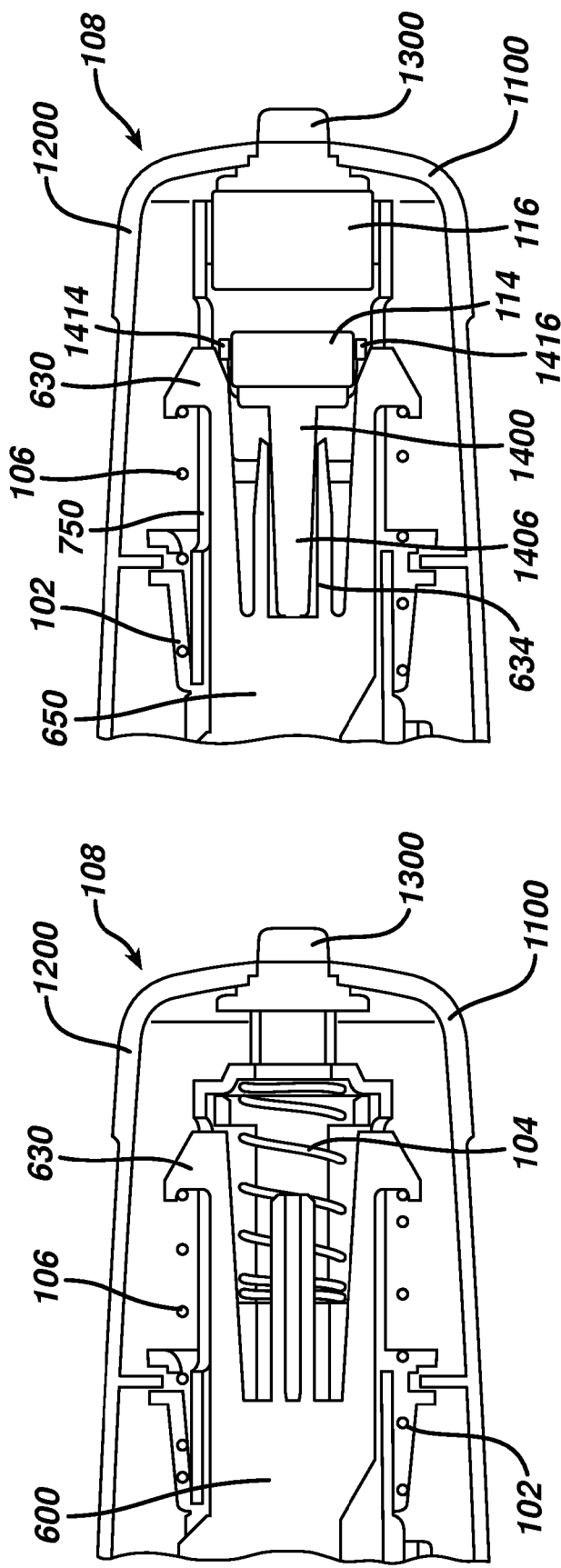

LANCING DEVICES AND METHODS

PRIORITY

This application claims the benefits of priority of U.S. Provisional Patent Application Ser. No. 61/052,088 filed on May 9, 2008.

BACKGROUND

Conventional lancing devices generally have a rigid housing, various operating mechanisms and a lancet that can be armed and launched so as to briefly protrude from one end of the lancing device. For example, conventional lancing devices can include a lancet that is mounted within a rigid housing such that the lancet is movable relative to the rigid housing along a longitudinal axis thereof. Typically, the lancet is spring loaded and launched, upon release of the spring, to penetrate (i.e., "lance") a target site (e.g., a dermal tissue target site). A bodily fluid sample (e.g., a whole blood sample) can then be expressed from the penetrated target site for collection and analysis.

Conventional lancing devices typically require a user to arm the lancing device, urge the lancing device against a target site, and then press a button or other switch to manually activate the lancing device such that a lancet within the device is launched (also referred to as "fired") towards the target site. The lancet then penetrates (e.g., lances) the target site, thereby creating an opening for the expression of a bodily fluid sample.

The arming and launching of conventional lancing devices involves a multitude of complicated mechanisms that result in the lancing device being relatively large in size, costly to manufacture and cumbersome to operate. In addition, the operation of conventional lancing device mechanisms can induce both vibrations within the lancing device and sounds that increase the level of pain perceived by a user.

SUMMARY OF THE DISCLOSURE

Applicants have recognized a need for a lancing device that is relatively inexpensive to manufacture and easily operated. Such device must also produce a minimal amount of vibration and/or sound during use, thereby decreasing the level of pain perceived by a user.

In view of the foregoing and in accordance with one aspect of the present invention, there is provided a lancing device that includes a housing, movable member, lancet, and a cap. The housing has spaced apart proximal and distal ends disposed along a longitudinal axis, and the housing is devoid of any actuator or button on its outer surface. The movable member is disposed in the housing and configured for movement along the longitudinal axis. The lancet is coupled to the moveable member. The cap encloses the lancet and has a plurality of fingers that extend along the longitudinal axis to engage the moveable member and move the moveable member towards the proximal end against a bias force such that at a predetermined position along the longitudinal axis, the plurality of fingers disengage from the moveable member to allow the moveable member to move in an opposite direction toward the distal end, thereby allowing the lancet to extend through the cap.

In yet a further aspect, a method of operating a lancing device is provided. The lancing device has a housing, moveable member, collar, lancet, and a cap. The housing has spaced apart distal and proximal ends disposed on a longitudinal axis. The moveable member has at least one arm extending along the longitudinal axis and disposed for movement along the longitudinal axis in the housing. The collar is in contact with the moveable member and configured to retain a lancet member. The cap has a plurality of fingers extending along the longitudinal axis into the housing. The method can be achieved by: pushing the at least one arm of the moveable member towards the proximal end against a bias member with the cap via at least one of the plurality of fingers of the cap with the lancet being disposed entirely within the cap; and disengaging the at least one arm of the moveable member from the at least one of the plurality of fingers of the cap to allow the bias member to push the movable member with the lancet toward the distal end through an aperture defined by a wall of the cap to extend from the cap.

In yet another aspect, a lancing device is provided that includes a lancing device having a housing, movable member, collar, lancet, rotatable ring, and a lancet depth adjustment. The housing has proximal and distal ends disposed along a longitudinal axis. The movable member is disposed in the housing and configured for movement along the longitudinal axis. The collar is partially disposed in the housing and coupled to the movable member so that the collar is movable as a unit with the movable member. The lancet is coupled to the collar. The rotatable ring is coupled to the collar. The lancet depth adjustment member is retained by both the rotatable ring and the collar so that the lancet depth adjustment member is rotatable relative to the housing to provide for a plurality of stop surfaces for the collar as the collar moves along the longitudinal axis to the distal end.

In yet another aspect, a lancing device is provided that includes first and second housings, movable member, bias member, lancet, depth adjustment member and a rotatable lock ring. The first housing is spaced apart proximal and distal ends disposed along a longitudinal axis. The second housing is disposed in the first housing in a fixed relationship with the first housing. The movable member is disposed in the second housing and configured for movement along the longitudinal axis. The bias member is located in the second housing to bias the moveable member in a direction towards the distal end. The lancet is coupled to the movable member so that the lancet moves as a unit with the movable member along the longitudinal axis. The depth adjustment member has a plurality of stop surfaces disposed radially about the longitudinal axis. The rotatable lock ring engages an inner surface of the first housing and an inner surface of the depth adjustment member to retain the depth adjustment member to the first housing in one radial position of the rotatable lock ring and to allow release of the depth adjustment member in another radial position of the rotatable lock ring relative to the longitudinal axis.

In yet a further aspect, a method of operating a lancing device is provided. The lancing device has a housing, moveable member, collar, lancet, and a cap. The housing includes spaced apart distal and proximal ends disposed on a longitudinal axis. The moveable member has at least one arm extending along the longitudinal axis and disposed for movement along the longitudinal axis in the housing. The collar is in contact with the moveable member and configured to retain the lancet. The cap has a plurality of fingers extending along the longitudinal axis into the housing. The method can be achieved by: pushing the at least one arm of the moveable member towards the proximal end against a bias member with the cap via at least one of the plurality of fingers of the cap with the lancet being disposed entirely within the cap; and disengaging the at least one arm of the moveable member from the at least one of the plurality of fingers of the cap to allow the bias member to push the movable member with the lancet toward the distal end through an aperture defined by a wall of the cap to extend from the cap.

In yet a further aspect, a method of operating a lancing device is provided. The lancing device has a housing, moveable member, lancet member with a lancet, and a cap. The housing includes spaced apart distal and proximal ends disposed on a longitudinal axis. The moveable member has at least one arm extending along the longitudinal axis and disposed for movement along the longitudinal axis in the housing. The lancet member is retained by the moveable member. The cap has at least one portion that extends along the longitudinal axis into the housing. The method can be achieved by: translating, with translation of the cap, the moveable member in a first direction along the longitudinal axis towards one of the ends; and accelerating the moveable member in a second direction opposite the first direction to extend the lancet beyond a periphery of the cap.

These and other embodiments, features and advantages will become apparent to those skilled in the art when taken with reference to the following more detailed description of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which:

FIGS. 4A-4B are perspective views of a lock ring, according to an exemplary embodiment described and illustrated herein.

FIGS. 6A-6B are perspective views of a movable member, according to an exemplary embodiment described and illustrated herein.

FIGS. 6C-6D are perspective views of another movable member, according to an exemplary embodiment described and illustrated herein.

FIGS. 8A-8B are perspective views of a second housing, according to an exemplary embodiment described and illustrated herein.

FIGS. 9A-9B are perspective views of a first housing bottom half, according to an exemplary embodiment described and illustrated herein.

FIGS. 10A-10B are perspective views of a first housing top half, according to an exemplary embodiment described and illustrated herein.

FIGS. 11A-11B are perspective views of a band, according to an exemplary embodiment described and illustrated herein.

FIGS. 13A-13D illustrate a sequence of steps used in capping and removing a lancet from a lancing device, according to an exemplary embodiment described and illustrated herein.

FIGS. 17A-17B illustrate alternative first bias members in a lancing device, according to embodiments described and illustrated herein.

DETAILED DESCRIPTION OF THE FIGURES

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
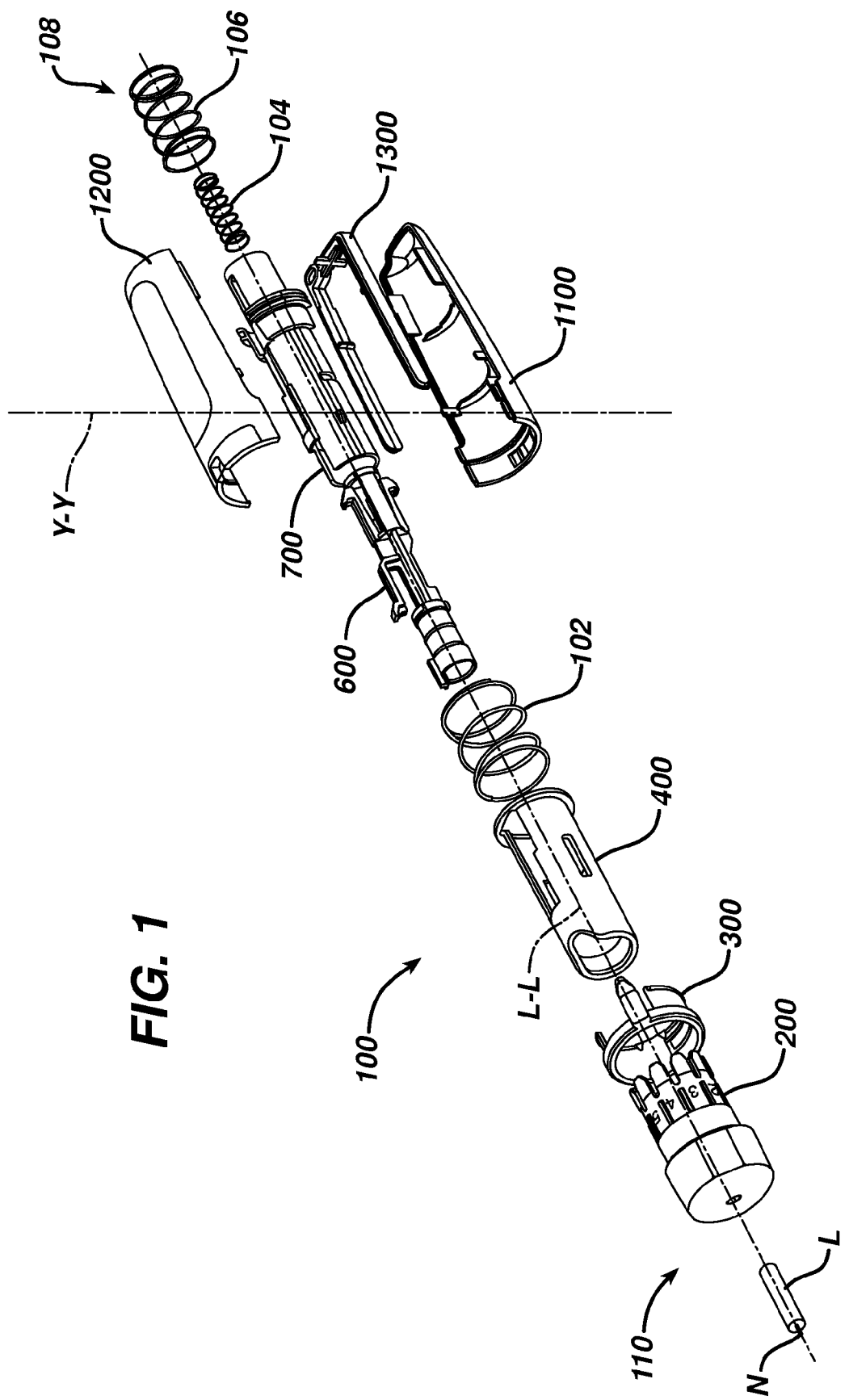
FIG. 1 is an exploded view of a lancing device, according to an exemplary embodiment described and illustrated herein.

FIG. 1 is an exploded view of lancing device 100, according to an exemplary embodiment described and illustrated herein. Lancing device 100 includes lancet depth adjustment member and cap 200, lock ring 300, collar 400, third bias member 102, movable member 600, first bias member 104, second housing 700, second bias member 106, first housing bottom 1100 (or alternately, a close-ended housing 1100'), first housing top 1200, and band 1300. Lancing device 100 includes lancing device proximal end 108 and lancing device distal end 110, and includes first housing top 1200 on the topside, and first housing bottom 1100 on the bottom side. When assembled, second housing 700, first housing bottom 1100, first housing top 1200, and band 1300 are fixedly attached to each other, while lancet depth adjustment member and cap 200, lock ring 300, collar 400, third bias member 102, movable member 600, first bias member 104, and second bias member 106 are attached, but free to move. As illustrated in the following figures, lancet depth adjustment member and cap 200, lock ring 300, collar 400, third bias member 102, movable member 600, second housing 700, second bias member 106, and band 1300 are assembled along an axis running from lancing device proximal end 108 to lancing device distal end 110, while first housing top 1200 and first housing bottom 1100 are assembled along an axis running perpendicular to an axis running from lancing device proximal end 108 to lancing device distal end 110. Lancet depth adjustment member and cap 200, lock ring 300, collar 400, third bias member 102, movable member 600, first bias member 104, second housing 700, second bias member 106, first housing bottom 1100, first housing top 1200, and band 1300 are generally snapped together, but can also be attached using adhesives or thermal bonding, such as, for example, ultrasonic welding. In an embodiment, first housing top 1200, band 1300, and first housing bottom 1100 are attached using ultrasonic welding along their points of contact. Tight clearances are maintained between the components of lancing device 100, typically in the range of 0.001-0.010". In an embodiment, movable member 600 travels inside second housing 700 along an axis between lancing device proximal end 108 and lancing device distal end 110, with a clearance of approximately 0.004".

As described in detail below, lancet depth adjustment member and cap 200, lock ring 300, collar 400, third bias member 102, movable member 600, first bias member 104, second housing 700, second bias member 106, first housing bottom 1100, first housing top 1200, and band 1300 are operatively connected such that a target site (e.g., a user's skin target site) can be lanced with a lancet (e.g., lancet L that includes lancet needle N) held within lancing device 100. In this regard, lancing device 100 is configured for launching lancet L such that lancet needle N lances a target site. Furthermore, lancet depth adjustment member and cap 200 is configured for a user to select (i.e., predetermine) needle penetration depth into a target site.

Lancing device 100 can be any suitable size but can be beneficially sized to fit within the palm of a user's hand and has, therefore, a typical but non-limiting length in the range of 50 mm to 70 mm and a typical but non-limiting width in the range of about 10 mm to about 20 mm. Such a compact size is beneficial in that it requires less storage space and is less conspicuous than conventionally sized lancing devices.

Figure 2:
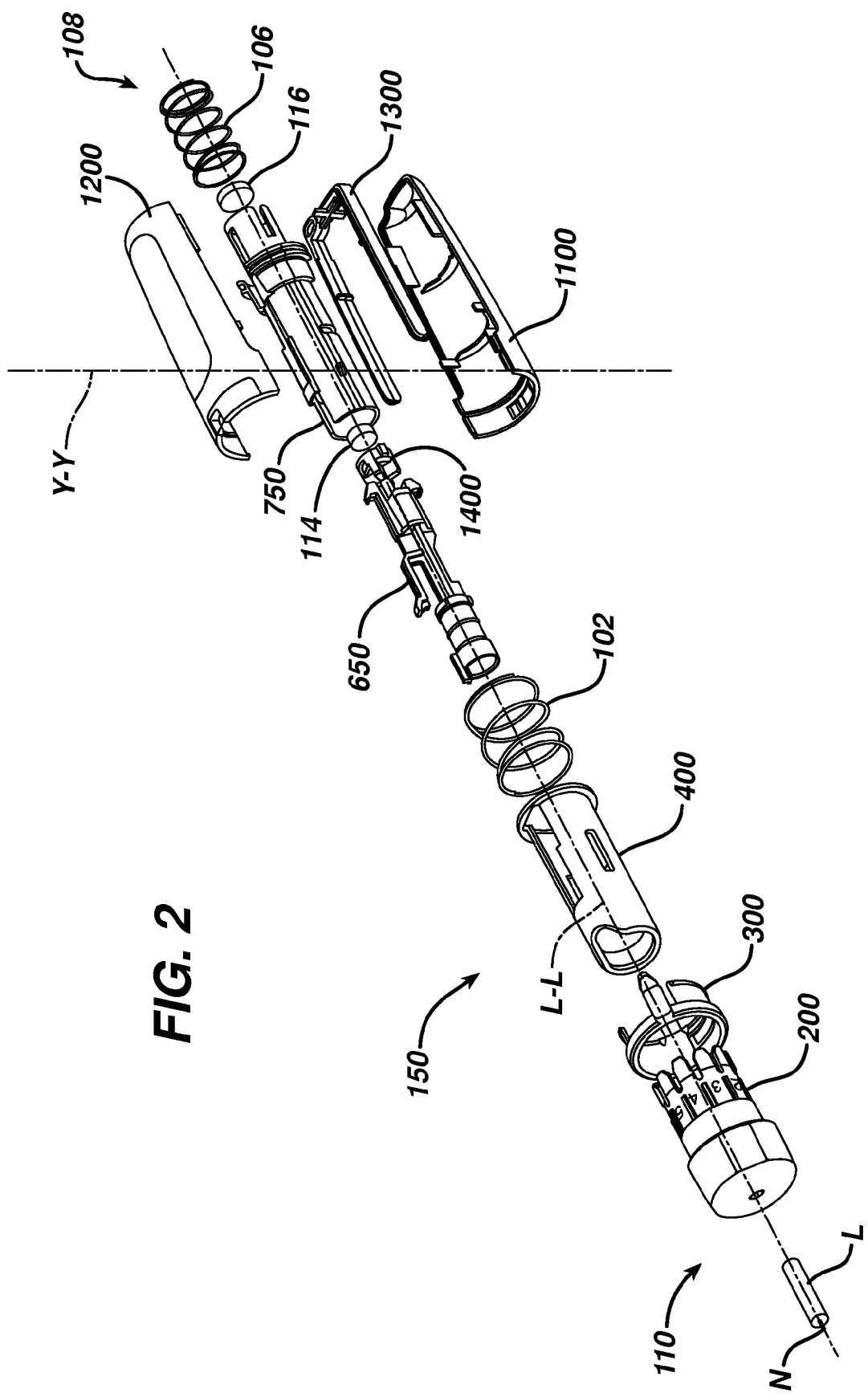
FIG. 2 is an exploded view of another lancing device, according to an exemplary embodiment described and illustrated herein.

FIG. 2 is an exploded view of another lancing device 150, according to an exemplary embodiment described and illustrated herein. Lancing device 150 uses magnetic forces to move the lancing device. Lancing device 150 includes lancet depth adjustment member and cap 200, lock ring 300, collar 400, third bias member 102, movable member 650, first bias member (comprising floating magnet holder 1400, floating magnet floating magnet 114, and fixed magnet 116), second housing 750, second bias member 106, first housing bottom 1100, first housing top 1200, and band 1300. Lancing device 150 includes lancing device proximal end 108 and lancing device distal end 110, and includes first housing top 1200 on the topside, and first housing bottom 1100 on the bottom side. When assembled, second housing 750, first housing bottom 1100, first housing top 1200, and band 1300 are fixedly attached to each other, while lancet depth adjustment member and cap 200, lock ring 300, collar 400, third bias member 102, movable member 650, first bias member (comprising floating magnet holder 1400, floating magnet floating magnet 114, and fixed magnet 116), and second bias member 106 are attached, but free to move. As illustrated in the following figures, lancet depth adjustment member and cap 200, lock ring 300, collar 400, third bias member 102, movable member 650, second housing 750, second bias member 106, and band 1300 are assembled along an axis running from lancing device proximal end 108 to lancing device distal end 110, while first housing top 1200 and first housing bottom 1100 are assembled along an axis running perpendicular to an axis running from lancing device proximal end 108 to lancing device distal end 110. Lancet depth adjustment member and cap 200, lock ring 300, collar 400, third bias member 102, movable member 650, first bias member (comprising floating magnet holder 1400, floating magnet 114, and fixed magnet 116), second housing 750, second bias member 106, first housing bottom 1100, first housing top 1200, and band 1300 are generally snapped together, but can also be attached using adhesives or thermal bonding, such as, for example, ultrasonic welding. In an embodiment, first housing top 1200, band 1300, and first housing bottom 1100 are attached using ultrasonic welding along their points of contact. Tight clearances are maintained between the components of lancing device 150, typically in the range of 0.001-0.010". In an embodiment, movable member 650 travels inside second housing 750 along an axis between lancing device proximal end 108 and lancing device distal end 110, with a clearance of approximately 0.004".

As described in detail below, lancet depth adjustment member and cap 200, lock ring 300, collar 400, third bias member 102, movable member 650, first bias member (comprising floating magnet holder 1400, floating magnet 114, and fixed magnet 116), second housing 750, second bias member 106, first housing bottom 1100, first housing top 1200, and band 1300 are operatively connected such that a target site (e.g., a user's skin target site) can be lanced with a lancet (e.g., lancet L that includes lancet needle N) held within lancing device 150. In this regard, lancing device 150 is configured for launching lancet L such that lancet needle N lances a target site. Furthermore, lancet depth adjustment member and cap 200 is configured for a user to select (i.e., predetermine) needle penetration depth into a target site.

Lancing device 150 can be any suitable size but can be beneficially sized to fit within the palm of a user's hand and has, therefore, a typical but non-limiting length in the range of 50 mm to 70 mm and a typical but non-limiting width in the range of about 10 mm to about 20 mm. Such a compact size is beneficial in that it requires less storage space and is less conspicuous than conventionally sized lancing devices.

Figure 3A:
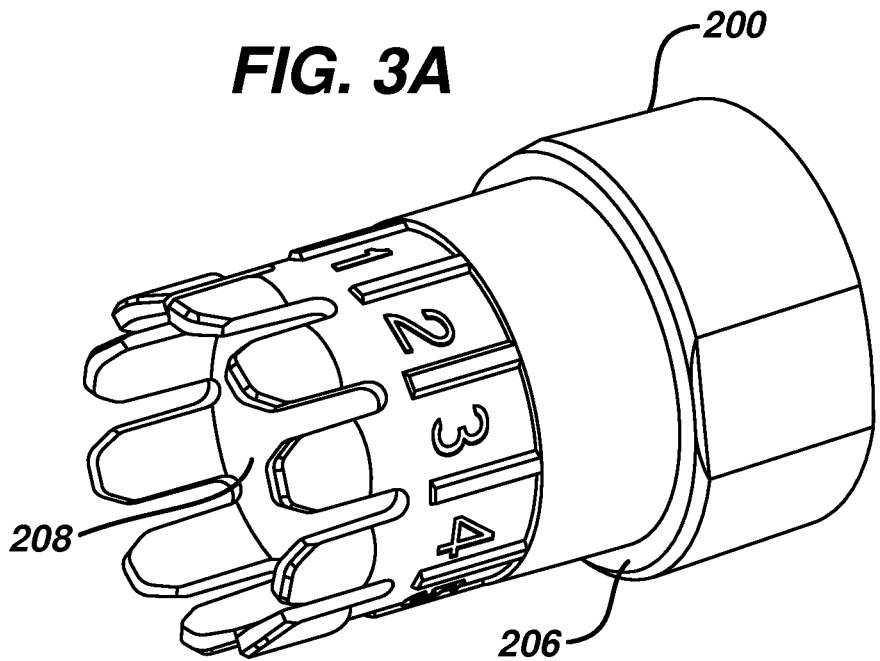
FIGS. 3A-3C are perspective views of a lancet depth adjustment member and cap, according to an exemplary embodiment described and illustrated herein.
Figure 3B:
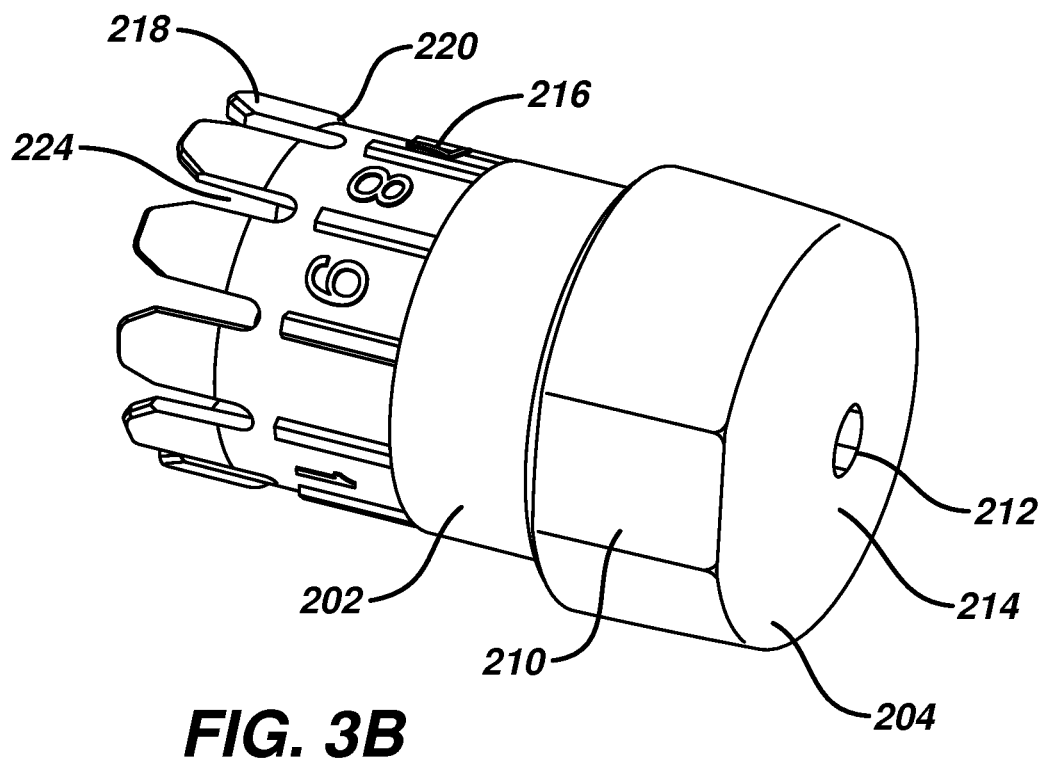
Figure 3C:
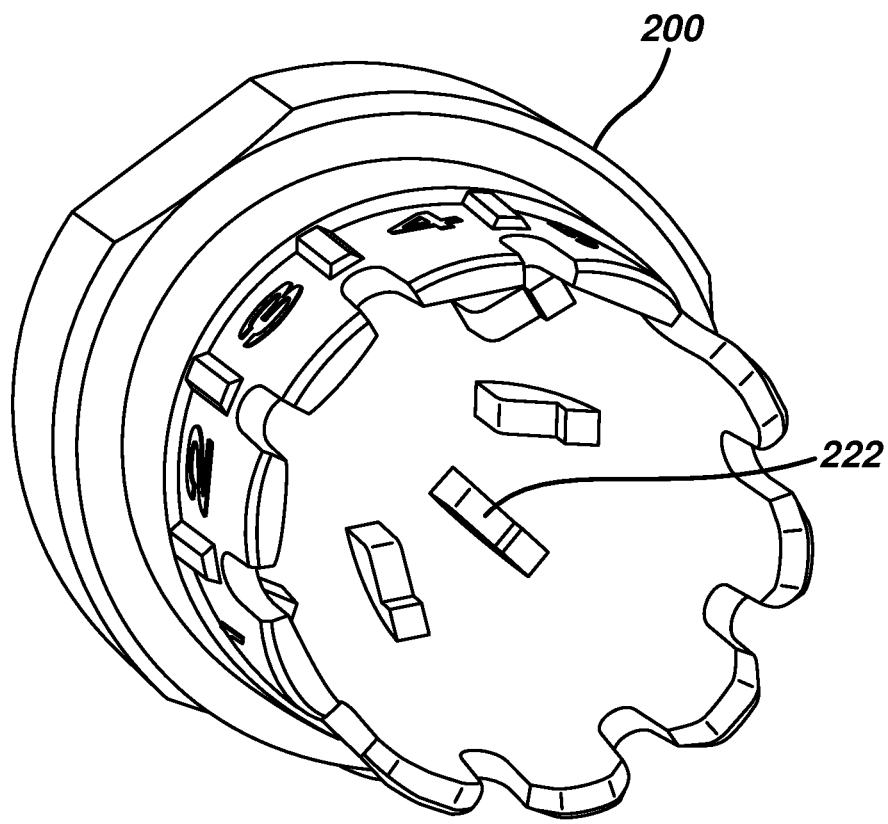

FIGS. 3A-3C are perspective views of lancet depth adjustment member and cap 200, according to an exemplary embodiment described and illustrated herein. Lancet depth adjustment member and cap 200 includes outside wall 202, front wall 204, stop 206, inside wall 208, grips 210, opening 212, contour 214, depth indicators 216, locking fingers 218, catches 220, depth stops 222, and pockets 224. In FIGS. 3A and 3B, lancet depth adjustment member and cap 200 includes outside wall 202, which is attached to front wall 204. Front wall 204 includes opening 212, through which a lancet needle can travel, and contour 214, which can shape the target site. Depth indicators 216 are used in conjunction with depth stops 222 (illustrated in FIG. 3C), in setting the depth of penetration of a lancet needle. Stop 206 stops against features in lock ring 300, such as, for example, outside edge 314, when lancing device 100 or lancing device 150 is being primed. Locking fingers 218 are distributed around the perimeter of lancet depth adjustment member and cap 200, and alternate with pockets 224. When locked in place, catches 220 interact with features on lock ring 300, such as, for example, pegs 312, preventing lancet depth adjustment member and cap 200 from being removed. When unlocked, pockets 224 are in line with pegs 312, allowing lancet depth adjustment member and cap 200 to be removed from lancing device 100 or lancing device 150. Lancet depth adjustment member and cap 200 include grips 210, making it easier to rotate lancet depth adjustment member and cap 200. Inside wall 208 travels over the outside surface of collar 400, with minimal clearance, allowing for smooth and precise motion. Lancet depth adjustment member and cap 200 can be at least partially clear or opaque, and can be made using rigid or flexible materials. For example, lancet depth adjustment member and cap 200 can be injection molded using rigid thermoplastics, such as, for example, ABS, polycarbonate, acrylic, or polystyrene, or it can be injection or reaction injection molded using thermoplastic or thermosetting elastomers.

FIGS. 4A-4B are perspective views of lock ring 300, according to an exemplary embodiment described and illustrated herein. Lock ring 300 includes grip 302, inside edge 304, guide 306, arm 308, catch 310, pegs 312, outside edge 314, inside surface 316, clasp 318, proximal end 324, and distal end 326. Grip 302 is used to rotate lock ring 300 about the axis that runs between lancing device proximal end 108 and lancing device distal end 110. Inside edge 304 rides against features first housing bottom 1100 and first housing top 1200, such as, for example, distal end 1106 and distal end 1204. Guide 306 positions lock ring 300 in features of first housing bottom 1100 and first housing top 1200, such as, for example, groove 1120 and groove 1218. Arm 308 and catch 310 extend from proximal end 324, and rotate into and out of contact with locking surface 638. When catch 310 is in contact with locking surface 638 it prevents movable member 600 or movable member 650 from moving, and when catch 310 is not in contact with locking surface 638, movable member 600 or movable member 650 are free to move along the axis between lancing device proximal end 108 and lancing device distal end 110. Lancet depth adjustment member and cap 200 is locked in place when pegs 312 interact with catches 220, preventing lancet depth adjustment member and cap 200 and locking fingers 218 from sliding out of lancing device 100 or lancing device 150. Lancet depth adjustment member and cap 200 is unlocked, and can be removed from lancing device 100 or lancing device 150, by rotating lock ring 300 so that pegs 312 are aligned with pockets 224. Outside edge 314 provides a stop for stop 206, when lancet depth adjustment member and cap 200 travels towards lancing device proximal end 108, establishing the maximum travel of lancet depth adjustment member and cap 200 towards lancing device proximal end 108. Inside surface 316 rotates about outside wall 202, while the outside surface of clasp 318 engages clasp pocket 1118. When lancing device 100 or lancing device 150 are assembled, proximal end 324 faces lancing device proximal end 108, while distal end 326 faces lancing device distal end 110. Lock ring 300 can be at least partially clear or opaque, and can be made using rigid or flexible materials. For example, lock ring 300 can be injection molded using rigid thermoplastics, such as, for example, ABS, polycarbonate, acrylic, or polystyrene, or it can be injection or reaction injection molded using thermoplastic or thermosetting elastomers.

Figure 5B:
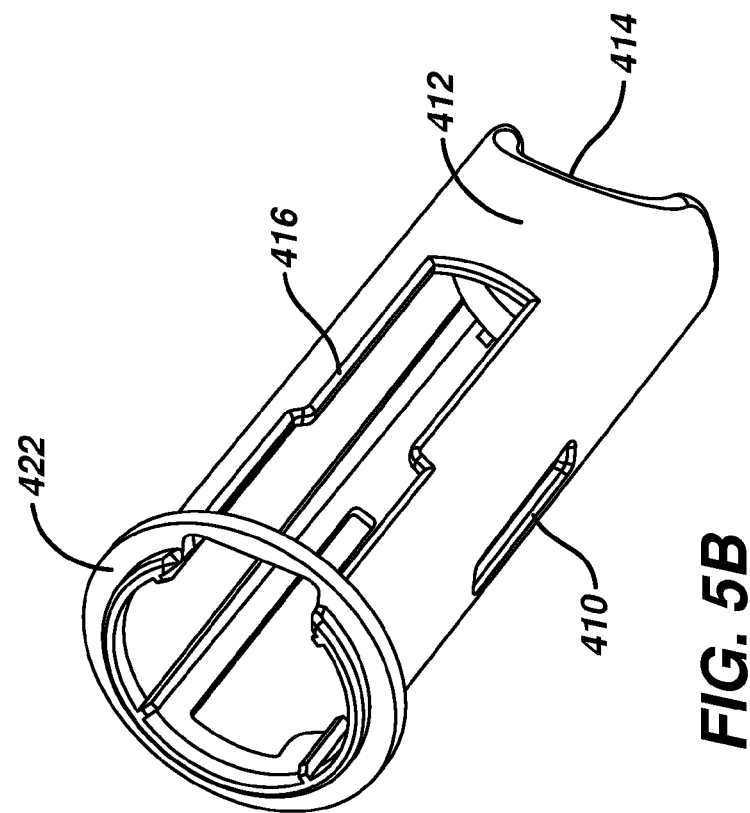
FIGS. 5A-5B are perspective views of a collar, according to an exemplary embodiment described and illustrated herein.
Figure 5A:
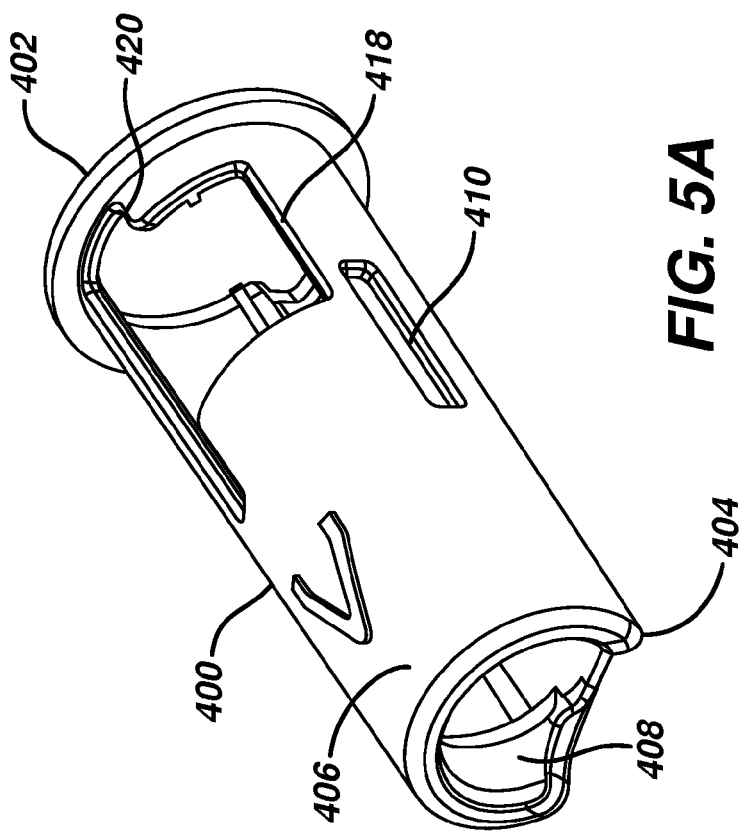

FIGS. 5A-5B are perspective views of collar 400, according to an exemplary embodiment described and illustrated herein. Collar 400 includes proximal end 402, distal end 404, bottom outside surface 406, inside surface 408, assembly windows 410, top outside surface 412, cutaway 414, top window 416, bottom window 418, catch window 420, and spring contact 422. When lancing device 100 or lancing device 150 are assembled, proximal end 402 faces lancing device proximal end 108, and distal end 404 faces lancing device distal end 110. Top outside surface 412 includes cutaway 414, which allows access to a lancet in movable member 600 or movable member 650, as illustrated in FIGS. 13 and 14. Top outside surface 412 also includes top window 416, which allows features such as, for example, priming arm 626, priming catch 629, and top landing 736 to clear top outside surface 412. Bottom outside surface 406 includes bottom window 418, which allows features such as, for example, catch 310 to clear bottom outside surface 406. Bottom window 418 includes catch window 420, which interacts with catch 310 to fix lock ring 300 in place when lancet depth adjustment member and cap 200 is removed. This is illustrated in FIGS. 12E-12F. Collar 400 includes inside surface 408, which rides along the outside surface of second housing 700 or second housing 750, when collar 400 travels along the axis between lancing device proximal end 108 and lancing device distal end 110. Collar 400 includes assembly windows 410, which interact with assembly pegs 732 during the assembly of lancing device 100 or lancing device 150, helping to position collar 400 relative to second housing 700 or second housing 750 during the assembly of lancing device 100 or lancing device 150. Spring contact 422 interacts with third bias member 102, biasing collar 400 in the direction of lancing device distal end 110, locking lock ring 300 in place by way of catch 310 and catch window 420 when lancet depth adjustment member and cap 200 is removed. Spring contact 422 and lancing device distal end 110 also allow collar 400 to travel back and forth along the axis between lancing device proximal end 108 and lancing device distal end 110 during the loading and unloading of lancets, during the prime and firing of lancing device 100 or lancing device 150, and while lancing device 100 or lancing device 150 return to their home positions. Collar 400 can be at least partially clear or opaque, and can be made using rigid or flexible materials. For example, collar 400 can be injection molded using rigid thermoplastics, such as, for example, ABS, polycarbonate, acrylic, or polystyrene, or it can be injection or reaction injection molded using thermoplastic or thermosetting elastomers.

FIGS. 6A-6B are perspective views of movable member 600, according to an exemplary embodiment described and illustrated herein. Movable member 600 includes distal end 602, proximal end 604, proximal bearings 606, distal bearings 608, launch spring housing 610, launch spring support 612, launch spring pin 613, stop tip 624, priming arm 626, priming catch 629, return arms 630, locking surface 638, lancet holder 640, expanding walls 642, ring 643, and ring groove 644. When assembling lancing device 100, proximal end 604 faces lancing device proximal end 108, while distal end 602 faces lancing device distal end 110. Proximal bearings 606 and distal bearings 608 make contact with the inside of second housing 700 when movable member 600 travels toward lancing device proximal end 108 or lancing device distal end 110. The clearance between proximal bearings 606, distal bearings 608, and the inside of second housing 700 is small (on the order of 0.001 to 0.010"), providing smooth, tight motion, as opposed to sloppy, loose motion. First bias member 104 is mounted inside launch spring housing 610, centered on launch spring pin 613 and resting upon launch spring support 612. First bias member 104 is free to expand and contract, and provides a motive force for moving movable member 600 back and forth along the axis between lancing device proximal end 108 and lancing device distal end 110. Stop tip 624 is connected to distal end 602 and interacts with features in lancet depth adjustment member and cap 200, such as, for example, depth stops 222, to limit the travel of movable member 600 towards lancing device distal end 110. In an embodiment, stop tip 624 is at least partially made with an acoustically dampened material, such as, for example, an elastomer, to minimize sound when firing lancing device 100. In other embodiments, features on lancet depth adjustment member and cap 200, such as, for example, depth stops 222, can also include acoustically dampened materials, such as, for example, an elastomer. Priming arm 626 and priming catch 629 are connected to movable member 600 and interact with features on lancet depth adjustment member and cap 200, such as, for example, locking fingers 218, when lancing device 100 is being primed and fired. Locking fingers 218 push priming catch 629 and movable member 600 toward lancing device proximal end 108 until priming catch 629 encounters firing ramp 1208. Firing ramp 1208 begins pushing priming catch 629 inward, away from locking fingers 218 until priming catch 629 clears locking fingers 218, allowing priming catch 629 and movable member 600 to rapidly travel towards lancing device distal end 110 during the firing cycle. While movable member 600 travels toward lancing device distal end 110 during the firing cycle, return arms 630 grip second bias member 106, compressing second bias member 106. Second bias member 106 provides the spring force to return movable member 600 to its home position after stop tip 624 has hit depth stops 222. Locking surface 638 interacts with catch 310 when lock ring 300 is rotated into its locked position, allowing lancet depth adjustment member and cap 200 to be removed and lancets to be loaded into lancet holder 640 while keeping movable member 600 fixed. Lancet holder 640 includes expanding walls 642, which expands when a lancet is inserted. Ring 643 (shown in FIG. 14E) sits in ring groove 644, limiting the extent to which expanding walls 642 can expand, and minimizing fatigue to expanding walls 642. Priming catch 629 and return arms 630 interact with features on second housing 700 to prevent rotation of movable member 600 about the axis running between lancing device proximal end 108 and lancing device distal end 110. Movable member 600 can be at least partially clear or opaque, and can be made using rigid materials. For example, movable member 600 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. In some embodiments lubricants are added to the thermoplastic, to minimize friction between movable member 600 and other parts, such as, for example, second housing 700. Conversely, lubricants can be added to the other parts, such as, for example, second housing 700, as long as the friction between movable member 600 and the other parts, such as, for example, second housing 700, remains small. Various lubricants can be used, such as, for example, fluoropolymers or silicones.

FIGS. 6C-6D are perspective views of movable member 650, according to an exemplary embodiment described and illustrated herein. Movable member 650 includes distal end 602, proximal end 604, proximal bearings 606, distal bearings 608, stop tip 624, priming arm 626, priming catch 629, return arms 630, magnet support 632, magnet holder guide 634, locking surface 638, lancet holder 640, expanding walls 642, ring 643, and ring groove 644. When assembling lancing device 150, proximal end 604 faces lancing device proximal end 108, while distal end 602 faces lancing device distal end 110. Proximal bearings 606 and distal bearings 608 make contact with the inside of second housing 750 when movable member 600 travels toward lancing device proximal end 108 or lancing device distal end 110. The clearance between proximal bearings 606, distal bearings 608, and the inside of second housing 750 is small (on the order of 0.001 to 0.010"), providing smooth, tight motion, as opposed to sloppy, loose motion. Floating magnet 114 is mounted into floating magnet holder 1400, while shaft 1406 rides in magnet holder guide 634 (as seen in FIG. 17B). When the elements of first bias member (comprising floating magnet holder 1400, floating magnet 114, and fixed magnet 116) are in close proximity, magnetic repulsion pushes floating magnet 114 away from fixed magnet 116, and provides a motive force for moving movable member 650 toward lancing device distal end 110.

Stop tip 624 is connected to distal end 602 and interacts with features in lancet depth adjustment member and cap 200, such as, for example, depth stops 222, to limit the travel of movable member 650 towards lancing device distal end 110. In an embodiment, stop tip 624 is at least partially made with an acoustically dampened material, such as, for example, an elastomer, to minimize sound when firing lancing device 150. In other embodiments, features on lancet depth adjustment member and cap 200, such as, for example, depth stops 222, can also include acoustically dampened materials, such as, for example, an elastomer. Priming arm 626 and priming catch 629 are connected to movable member 650 and interact with features on lancet depth adjustment member and cap 200, such as, for example, locking fingers 218, when lancing device 150 is being primed and fired. Locking fingers 218 push priming catch 629 and movable member 650 toward lancing device proximal end 108 until priming catch 629 encounters firing ramp 1208. Firing ramp 1208 begins pushing priming catch 629 inward, away from locking fingers 218 until priming catch 629 clears locking fingers 218, allowing priming catch 629 and movable member 650 to rapidly travel towards lancing device distal end 110 during the firing cycle. While movable member 650 travels toward lancing device distal end 110 during the firing cycle, return arms 630 grip second bias member 106, compressing second bias member 106. Second bias member 106 provides the spring force to return movable member 650 to its home position after stop tip 624 has hit depth stops 222. Locking surface 638 interacts with catch 310 when lock ring 300 is rotated into its locked position, allowing lancet depth adjustment member and cap 200 to be removed and lancets to be loaded into lancet holder 640 while keeping movable member 650 fixed. Lancet holder 640 includes expanding walls 642, which expands when a lancet is inserted. Ring 643 (shown in FIG. 14E) sits in ring groove 644, limiting the extent to which expanding walls 642 can expand, and minimizing fatigue to expanding walls 642. Priming catch 629 and return arms 630 interact with features on second housing 750 to prevent rotation of movable member 650 about the axis running between lancing device proximal end 108 and lancing device distal end 110. Movable member 650 can be at least partially clear or opaque, and can be made using rigid materials. For example, movable member 650 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. In some embodiments lubricants are added to the thermoplastic, to minimize friction between movable member 650 and other parts, such as, for example, second housing 750. Conversely, lubricants can be added to the other parts, such as, for example, second housing 750, as long as the friction between movable member 650 and the other parts, such as, for example, second housing 750, remains small. Various lubricants can be used, such as, for example, fluoropolymers or silicones.

Figure 7B:
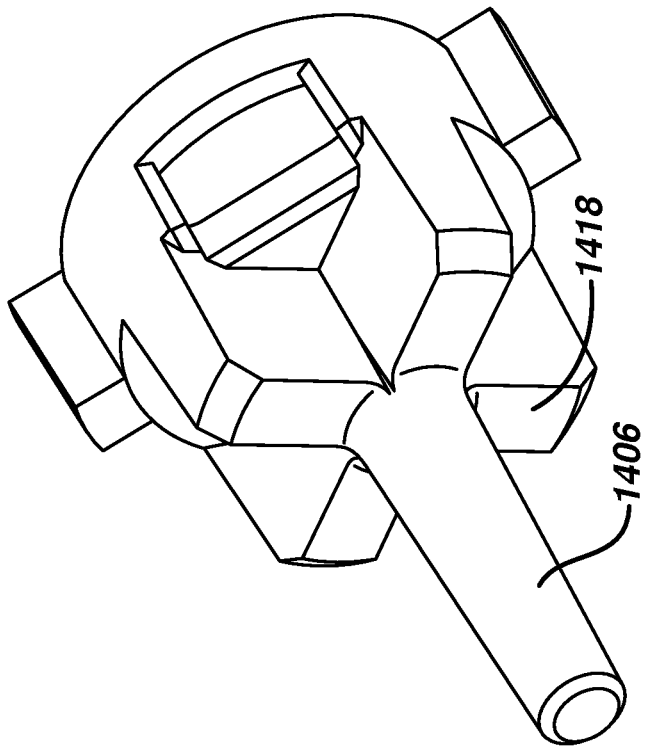
FIGS. 7A-7B are perspective views of a floating magnet holder, according to an exemplary embodiment described and illustrated herein.
Figure 7A:
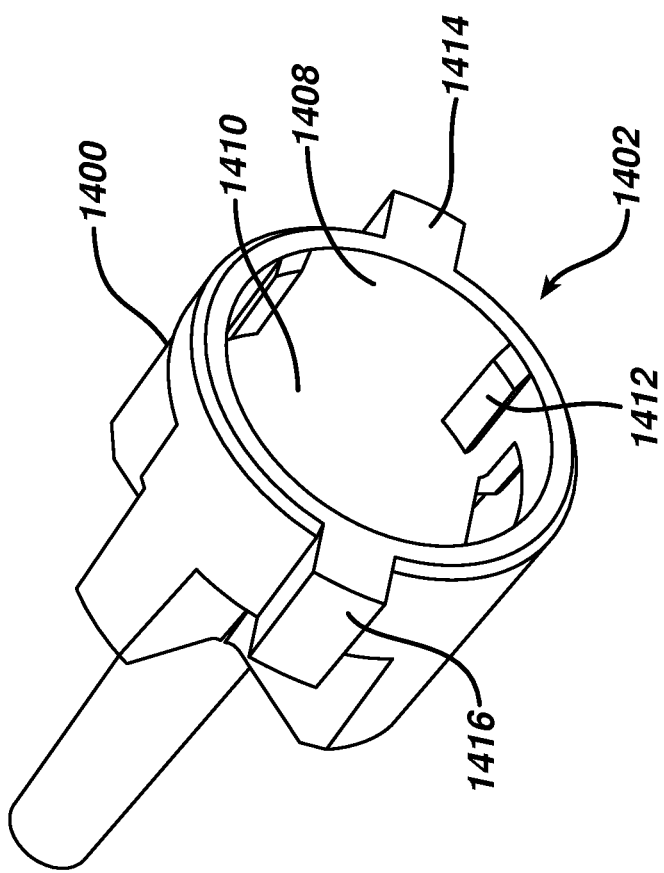

FIGS. 7A-7B are perspective views of floating magnet holder 1400, according to an exemplary embodiment described and illustrated herein. Floating magnet holder 1400 includes proximal end 1402, distal end 1404, shaft 1406, wall 1408, bottom 1410, ribs 1412, lower finger 1414, upper finger 1416, and contact surfaces 1418. During assembly, floating magnet 114 is pressed into proximal end 1402 until it seats against bottom 1410. Floating magnet 114 is retained in proximal end 1402 by ribs 1412. Shaft 1406 is inserted into magnet holder guide 634, and is free to travel towards distal end 602 and proximal end 604. When floating magnet holder 1400 travels toward lancing device distal end 110, contact surfaces 1418 makes contact with magnet support 632, driving 65 forward. Eventually lower finger 1414 and upper finger 1416 hit second housing 750 limiting the travel of floating magnet holder 1400. At that point, movable member 650 loses contact with floating magnet holder 1400 and travels toward lancing device distal end 110 due to its forward momentum. Floating magnet holder 1400 can be at least partially clear or opaque, and can be made using rigid materials. For example, floating magnet holder 1400 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. In some embodiments lubricants are added to the thermoplastic, to minimize friction between floating magnet holder 1400 and other parts, such as, for example, movable member 650. Conversely, lubricants can be added to the other parts, such as, for example, movable member 650, as long as the friction between floating magnet holder 1400 and the other parts, such as, for example, movable member 650, remains small. Various lubricants can be used, such as, for example, fluoropolymers or silicones.

FIGS. 8A-8B are perspective views of second housing 700, according to an exemplary embodiment described and illustrated herein. Second housing 700 includes distal end 702, top 703, proximal end 704, 705, inner surface 706, priming window 714, return windows 716, stop window 718, mandrels 722, positioning grooves 724, lock window 730, assembly pegs 732, and top landing 736. When assembled, proximal end 704 faces lancing device proximal end 108, while distal end 702 faces lancing device distal end 110. FIG. 8A illustrates features on top 703, while FIG. 8B illustrates features on 705. Second housing 700 includes inner surface 706 which extends from proximal end 704 to distal end 702 and provides smooth contact surfaces for mating parts, such as, for example, proximal bearings 606 and distal bearings 608. Priming window 714, return windows 716, stop window 718, and lock window 730 provide access between the inside and outside of second housing 700, and in some cases provide contact surfaces that register other parts to second housing 700. Positioning grooves 724 interact with features in first housing bottom 1100 and first housing top 1200, such as, for example, positioning ribs 1110 and positioning ribs 1206. Mandrels 722 provides inside support for third bias member 102 and second bias member 106, while return windows 716 allow return arms 630 to grip second bias member 106. Priming window 714 provides clearance for priming catch 629, return windows 716 provides clearance for return arms 630, stop window 718 provides clearance for stop tip 624, and lock window 730 provides clearance for catch 310. Top landing 736 mates with features on collar 400, such as, for example, top window 416, and prevents collar 400 from rotating about the axis between lancing device proximal end 108 and 110. Assembly pegs 732 are used in the assembly of lancing device 100, and serve no purpose after assembly. Second housing 700 can be at least partially clear or opaque, and can be made using rigid materials. For example, second housing 700 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof In some embodiments lubricants are added to the thermoplastic, to minimize friction between second housing 700 and other parts, such as, for example, movable member 600. Conversely, lubricants can be added to the other parts, such as, for example, movable member 600, as long as the friction between second housing 700 and the other parts, such as, for example, movable member 600, remains small. Various lubricants can be used, such as, for example, fluoropolymers or silicones.

Figure 8C:
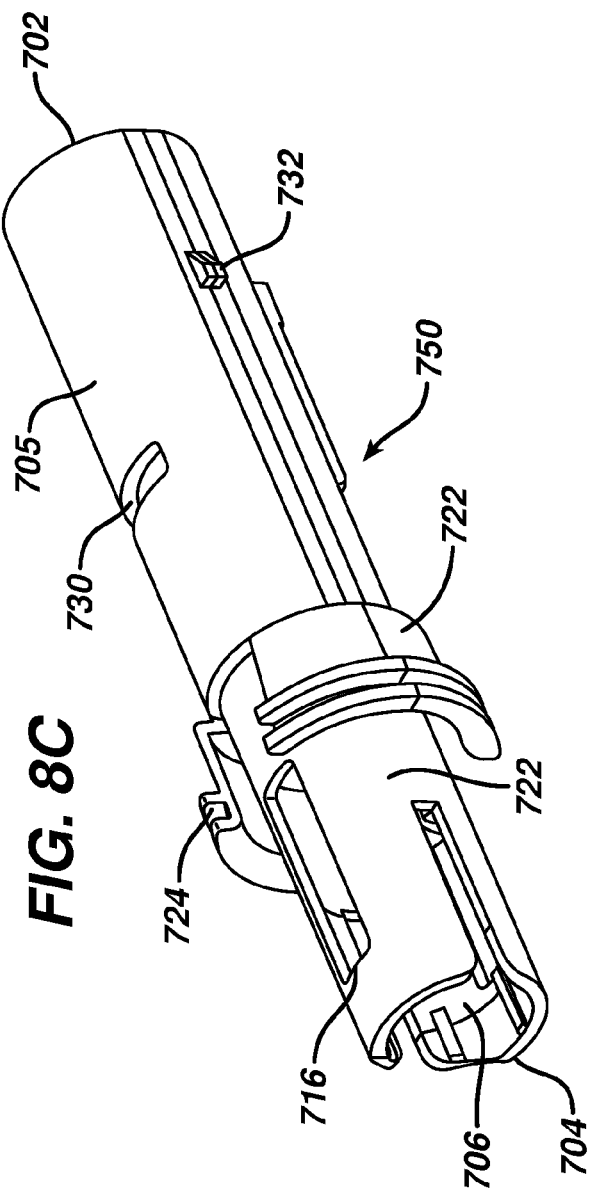
FIGS. 8C-8D are perspective views of another second housing, according to an exemplary embodiment described and illustrated herein.
Figure 8D:
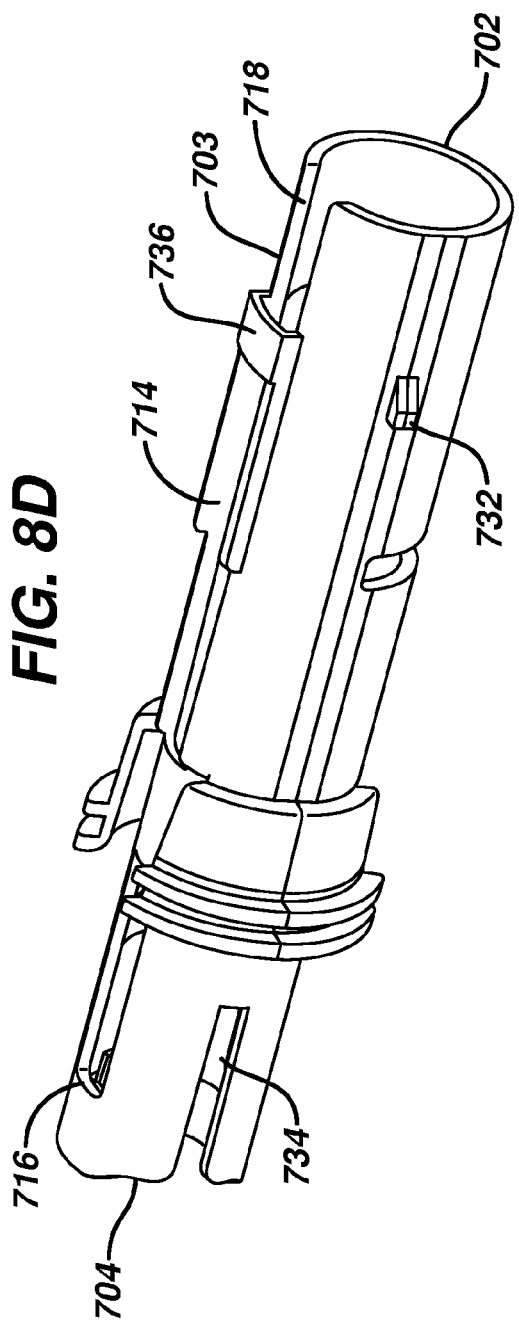

FIGS. 8C-8D are perspective views of second housing 750, according to an exemplary embodiment described and illustrated herein. Second housing 750 includes distal end 702, top 703, proximal end 704, 705, inner surface 706, priming window 714, return windows 716, stop window 718, mandrels 722, positioning grooves 724, lock window 730, assembly pegs 732, and top landing 736. When assembled, proximal end 704 faces lancing device proximal end 108, while distal end 702 faces 110. FIG. 8D illustrates features on top 703, while FIG. 8C illustrates features on 705. Second housing 750 includes inner surface 706 which extends from proximal end 704 to distal end 702 and provides smooth contact surfaces for mating parts, such as, for example, proximal bearings 606 and distal bearings 608. Priming window 714, return windows 716, stop window 718, lock window 730, and magnet holder windows 734 provide access between the inside and outside of second housing 750, and in some cases provide contact surfaces that register other parts to second housing 750. Positioning grooves 724 interact with features in first housing bottom 1100 and first housing top 1200, such as positioning ribs 1110 and positioning ribs 1206. Mandrels 722 provides inside support for third bias member 102 and second bias member 106, while return windows 716 allow return arms 630 to grip second bias member 106. Priming window 714 provides clearance for priming catch 629, return windows 716 provides clearance for return arms 630, stop window 718 provides clearance for stop tip 624, lock window 730 provides clearance for catch 310, and magnet holder windows 734 provide clearance for lower finger 1414 and upper finger 1416. Top landing 736 mates with features on collar 400, such as, for example, top window 416, and prevents collar 400 from rotating about the axis between lancing device proximal end 108 and lancing device distal end 110. Assembly pegs 732 are used in the assembly of lancing device 150, and serve no purpose after assembly. Second housing 750 can be at least partially clear or opaque, and can be made using rigid materials. For example, second housing 750 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. In some embodiments lubricants are added to the thermoplastic, to minimize friction between second housing 750 and other parts, such as movable member 650. Conversely, lubricants can be added to the other parts, such as movable member 650, as long as the friction between second housing 750 and the other parts, such as movable member 650, remains small. Various lubricants can be used, such as, for example, fluoropolymers or silicones.

FIGS. 9A-9B are perspective views of first housing bottom 1100, according to an exemplary embodiment described and illustrated herein. First housing bottom 1100 includes grip 1102, distal end 1106, proximal end 1108, positioning ribs 1110, outside surface 1112, inside surface 1114, fastening ribs 1116, clasp pocket 1118, and groove 1120. When assembled, proximal end 1108 is placed at lancing device proximal end 108, while distal end 1106 is placed facing lancing device distal end 110. Outside surface 1112 includes grip 1102, which allows for enhanced handling of lancing device 100 or lancing device 150, and in the embodiment illustrated in FIG. 11 is made by molding a recess in outside surface 1112. Other embodiments could include the use of additional materials, such as, for example, over-molded elastomers. Inside surface 1114 includes positioning ribs 1110, which are located at various points along inside surface 1114 and interact with the outer surface of second housing 700 or second housing 750, positioning second housing 700 or second housing 750 in a stationary and precise location within first housing bottom 1100. First housing bottom 1100 also includes fastening ribs 1116, which can be used in fastening first housing bottom 1100 to first housing top 1200 and/or band 1300, using methods such as, for example, ultrasonic welding. Groove 1120 mates with features on lock ring 300, such as guide 306, precisely positioning lock ring 300 and allowing rotation of lock ring 300 about the axis between lancing device proximal end 108 and lancing device distal end 110. Clasp pocket 1118 interacts with features on lock ring 300, such as clasp 318, tensioning clasp 318 against clasp pocket 1118 and providing a smooth fit between lock ring 300 and first housing bottom 1100. First housing bottom 1100 can be at least partially clear or opaque, and can be made using rigid materials. For example, first housing bottom 1100 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. First housing bottom 1100 can also be formed of semi-rigid materials including, for example, polypropylene, high-density polyethylene, polyurethane, ethylene propylene rubber, polymethylpentene and combinations thereof.

FIGS. 10A-10B are perspective views of first housing top 1200, according to an exemplary embodiment described and illustrated herein. First housing top 1200 includes proximal end 1202, distal end 1204, depth window 1205, positioning ribs 1206, firing ramp 1208, grip 1210, outside surface 1212, inside surface 1214, fastening ribs 1216, groove 1218. When assembled, proximal end 1202 is placed at lancing device proximal end 108, while distal end 1204 is placed facing lancing device distal end 110. Outside surface 1212 includes grip 1210, which allows for enhanced handling of lancing device 100 or lancing device 150, and in the embodiment illustrated in FIG. 12 is made by molding a recess in outside surface 1212. Other embodiments could include the use of additional materials, such as, for example, over-molded elastomers. Inside surface 1214 includes positioning ribs 1206, which are located at various points along inside surface 1214 and interact with the outer surface of second housing 700 or second housing 750, positioning second housing 700 or second housing 750 in a stationary and precise location within first housing top 1200. First housing top 1200 also includes fastening ribs 1216, which can be used in fastening first housing top 1200 to first housing bottom 1100 and/or band 1300, using methods such as, for example, ultrasonic welding. Groove 1218 mates with features on lock ring 300, such as guide 306, precisely positioning lock ring 300 and allowing rotation of lock ring 300 about the axis between lancing device proximal end 108 and lancing device distal end 110. Firing ramp 1208 interacts with features on movable member 600 or movable member 650, such as priming catch 629, pushing priming catch 629 away from locking fingers 218 at the instant lancing device 100 or lancing device 150 is fired. Depth window 1205 allows depth indicators 216 to be viewed, when lancet depth adjustment member and cap 200 sets the depth of lancet penetration. First housing top 1200 can be at least partially clear or opaque, and can be made using rigid materials. For example, first housing top 1200 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. First housing top 1200 can also be formed of semi-rigid materials including, for example, polypropylene, high-density polyethylene, polyurethane, ethylene propylene rubber, polymethylpentene and combinations thereof.

FIGS. 11A-11B are perspective views of band 1300, according to an exemplary embodiment described and illustrated herein. Eyelet 1302 provides a fastening point for key rings or other optional accessories. Band 1300 can be at least partially clear or opaque, and can be made using rigid materials. For example, band 1300 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. Band 1300 can also be formed of semi-rigid materials including, for example, polypropylene, high-density polyethylene, polyurethane, ethylene propylene rubber, polymethylpentene and combinations thereof.

Having described various components of lancing device 100 and lancing device 150, details of the interaction and functioning of such components will now be described with reference to FIGS. 12 through 18.

Figure 12A:
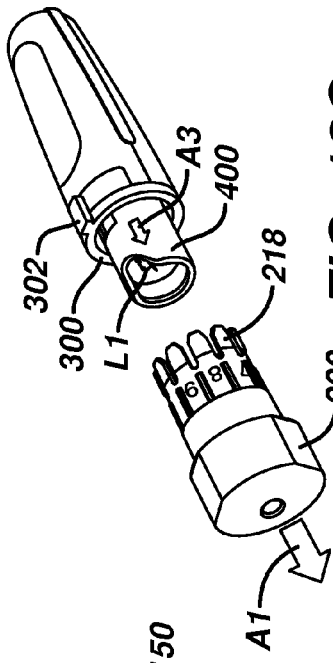
FIGS. 12A-12G illustrate a sequence of steps used in removing a lancet depth adjustment member and cap from a lancing device, according to an exemplary embodiment described and illustrated herein.
Figure 12B:
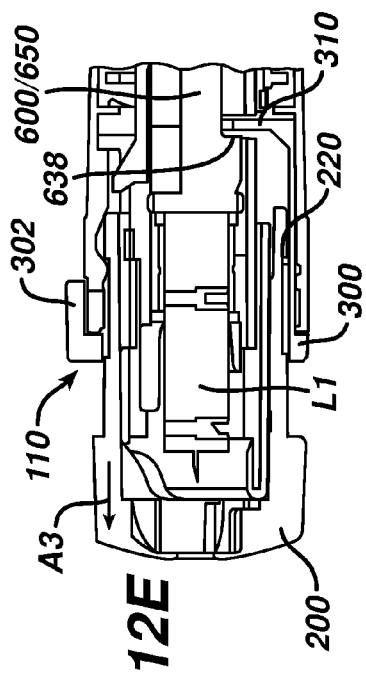
Figure 12C:
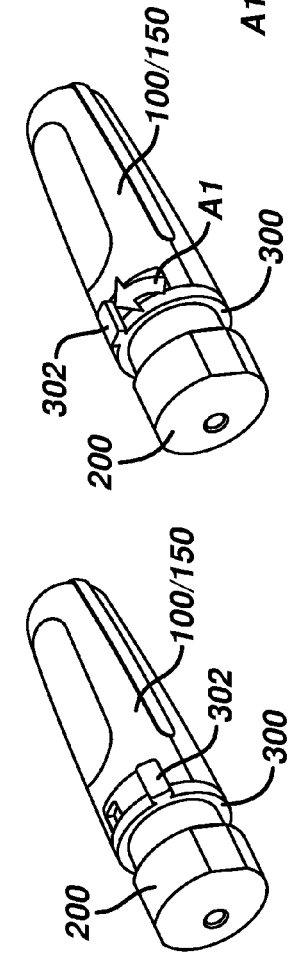
Figure 12D:
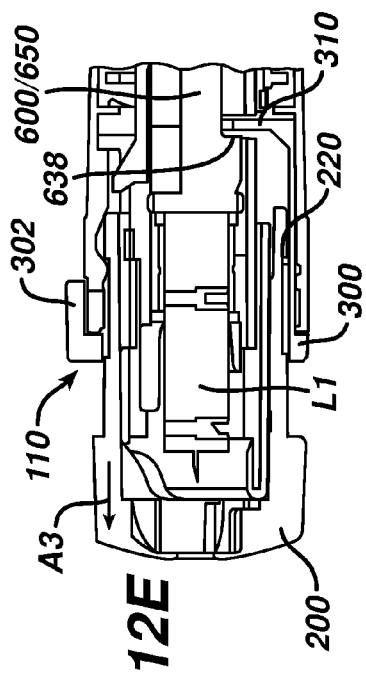
Figure 12E:
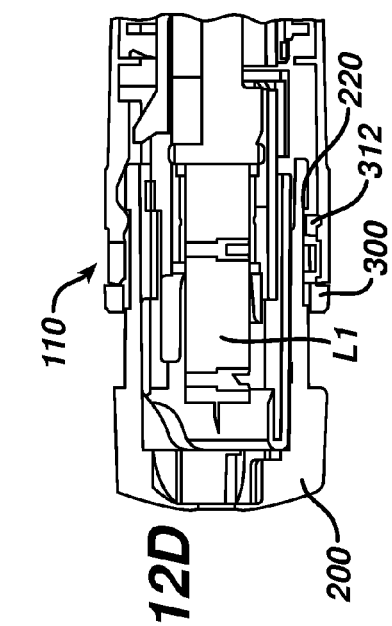
Figure 12F:
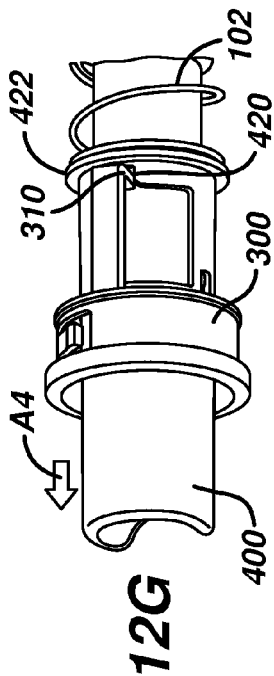
Figure 12G:
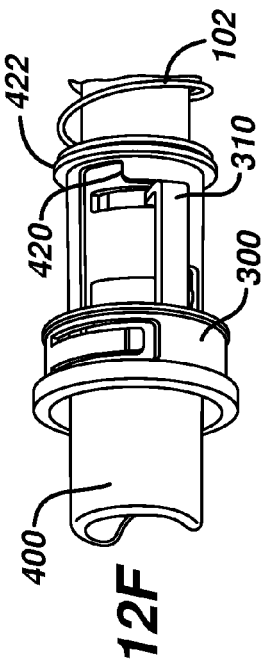

FIGS. 12A-12G illustrate a sequence of steps used in removing a lancet depth adjustment member and cap from lancing device 100 or lancing device 150, according to an exemplary embodiment described and illustrated herein. In FIG. 12A, lancing device 100 or lancing device 150 is in the home position. Lancet depth adjustment member and cap 200 is locked in place, since grip 302 is in the locked position. In FIG. 12B, grip 302 is rotated, in the direction of arrow Al, into an unlocked position. In this position, lancet depth adjustment member and cap 200 can be removed from lancing device 100 or lancing device 150, as indicated by arrow A2 in FIG. 12C. When lancet depth adjustment member and cap 200 is removed from lancing device 100 or lancing device 150, collar 400 moves forward, as indicated by arrow A3, and lancet L1 is exposed. When grip 302 is moved into the unlocked position, as illustrated by FIG. 12B, locking fingers 218 disengage from lock ring 300. FIG. 12D is a cross sectional view of lancing device distal end 110 at the stage illustrated in FIG. 12A. In FIG. 12D, catches 220 are in contact with pegs 312, preventing lancet depth adjustment member and cap 200 from being removed from lancing device distal end 110. FIG. 12E is a cross sectional view of lancing device distal end 110 at the stage illustrated in FIG. 12B. In FIG. 12E, grip 302 has been rotated into an unlocked position, and lancet depth adjustment member and cap 200 can be removed by pulling it out of lancing device distal end 110 in the direction of arrow A3. As grip 302 is moved into the unlocked position, catch 310 rotates into proximity with locking surface 638, preventing movable member 600 or movable member 650 from moving towards lancing device proximal end 108 when replacing lancet L1. When grip 302 is rotated, pegs 312 rotate away from catches 220, allowing lancet depth adjustment member and cap 200 to be moved away from lancing device distal end 110. FIG. 12F is a partial assembly view of lancing device distal end 110 at the stage illustrated in FIG. 12A. In FIG. 12F, grip 302 is still in the locked position, and catch 310 has not engaged with catch window 420. Third bias member 102 pushes collar 400 toward lancing device distal end 110, but catch 310 is free to rotate. FIG. 12 G is a partial assembly view of lancing device distal end 110 at the stage illustrated in FIG. 12C. In FIG. 12G, grip 302 has been moved into an unlocked position, lancet depth adjustment member and cap 200 has been removed from lancing device distal end 110, and catch 310 engages catch window 420. Third bias member 102 pushes collar 400 in the direction indicated by arrow A4, and catch 310 prevents lock ring 300 from being rotated when lancet depth adjustment member and cap 200 has been removed from lancing device distal end 110.

FIGS. 13A-13D illustrate a sequence of steps used in capping and removing a lancet from lancing device 100 or lancing device 150, according to an exemplary embodiment described and illustrated herein. In FIG. 13A, lancing device 100 or lancing device 150 is in the stage illustrated in FIG. 12C. Lancet L1 is inside collar 400, and needs to be replaced. New lancet L2 with cap C2 are moved in the direction indicated by arrow A5. In FIG. 13B, lancet L2 and cap C2 continue to move in the direction of arrow A6, while collar 400 begins to move in the direction indicated by arrow A7. Lancet L2 is positioned in cutaway 414, while cap C2 seats on lancet L1. In FIG. 13C, the assembly of lancet L1, cap C2, and lancet L2 is removed from lancing device 100 or lancing device 150, and collar 400 springs back in the direction indicated by arrow A8. FIG. 13D is a cross sectional view of lancing device distal end 110 at the stage illustrated in FIG. 13B. In FIG. 13D, cap C2 has been moved in the direction indicated by arrow A6 and is attached to used lancet L1. Catch 310 catches against locking surface 638, preventing movable member 600 or movable member 650 from moving toward lancing device proximal end 108. Collar 400 moves in the direction indicated by arrow A7 as cap C2 seats on lancet L1, but is limited in motion.

Figure 14C:
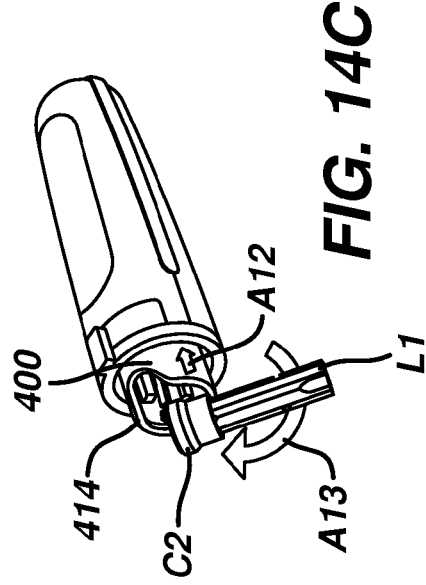
FIGS. 14A-14E illustrate a sequence of steps used in loading a lancet into a lancing device, according to an exemplary embodiment described and illustrated herein.
Figure 14E:
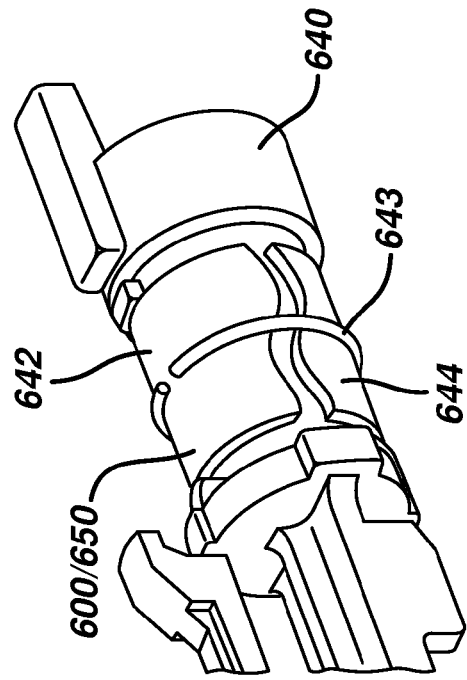
Figure 14B:
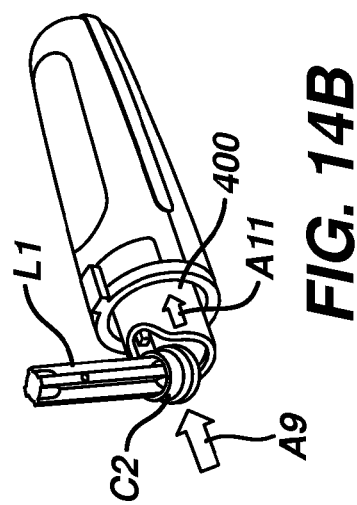
Figure 14A:
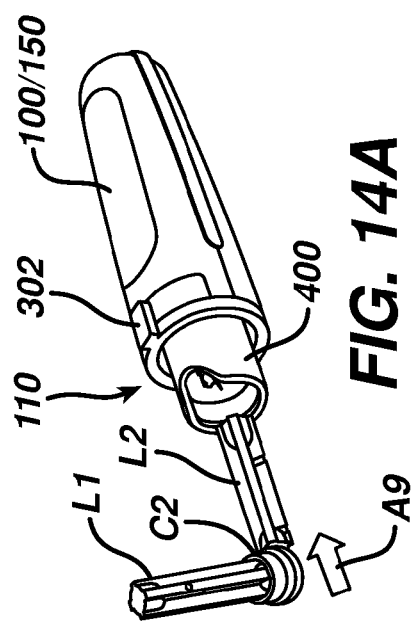
Figure 14D:
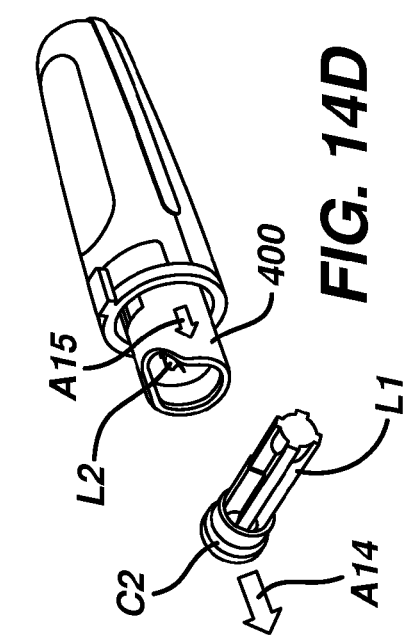

FIGS. 14A-14E illustrate a sequence of steps used in loading a lancet into lancing device 100 or lancing device 150, according to an exemplary embodiment described and illustrated herein. In FIG. 14A, the lancet assembly from FIG. 13C is rotated so that new lancet L2 faces lancing device 100 or lancing device 150. Lancet L2 is moved towards lancing device 100 or lancing device 150, as indicated by arrow A9. In FIG. 14B, lancet L2 is inserted into collar 400 and lancet holder 640 (as illustrated in FIG. 14E), as indicated by arrow A10. As contact is made, collar 400 moves back, as indicated by arrow A11. Once lancet L2 is fully seated, lancet L1 is rotated as indicated by arrow A13 in FIG. 14C. Rotating lancet L1 breaks cap C2 free from lancet L2, allowing lancet L1 and cap C2 to be removed from lancet L2. As lancet L1 and cap C2 are rotated, collar 400 pushes further back, away from lancet L1 and cap C2, as indicated by arrow A12. Once cap C2 breaks free from lancet L2, the assembly of cap C2 and lancet L1 can be removed, and disposed of, as indicated by arrow A14 in FIG. 14D. As illustrated in FIG. 14D, collar 400 springs back, in the direction indicated by arrow A15, and lancet L2 is ready for use. As collar 400 springs back to its home position, as illustrated in FIG. 14D, lancet L2, and its needle, are protected from inadvertent contact by collar 400. FIG. 14E is a partial assembly view of lancing device distal end 110 at the stage illustrated in FIG. 14A, before insertion of lancet L2. As illustrated in FIG. 14E, movable member 600 or movable member 650 include lancet holder 640 and expanding walls 642. Expanding walls 642 includes ring 643 in ring groove 644. Ring 643 prevents fatigue in expanding walls 642 when lancets are inserted and removed from lancet holder 640.

Figure 15A:
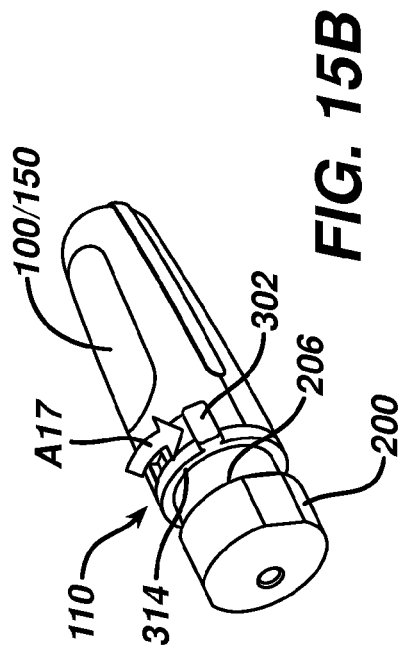
FIGS. 15A-15C illustrate a sequence of steps used in attaching a lancet depth adjustment member and cap to a lancing device and setting its depth of penetration, according to an exemplary embodiment described and illustrated herein.
Figure 15B:
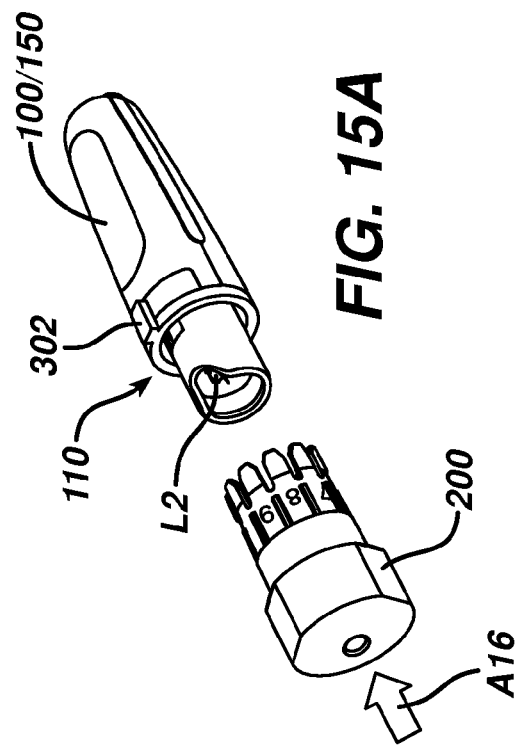
Figure 15C:
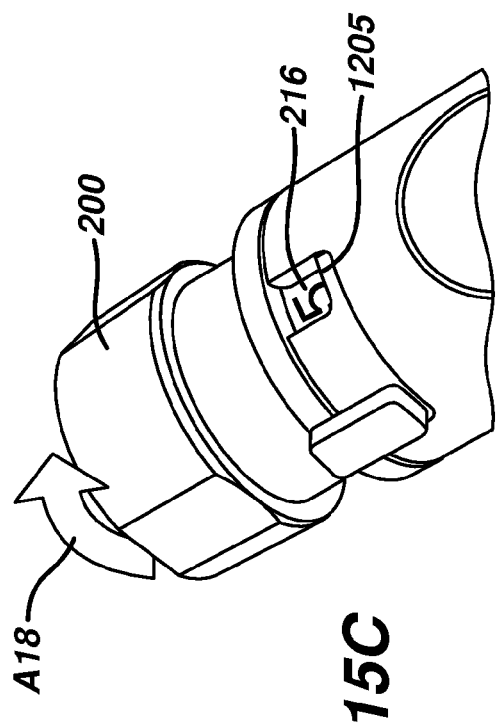

FIGS. 15A-15C illustrate a sequence of steps used in attaching a lancet depth adjustment member and cap to lancing device 100 or lancing device 150 and setting their depth of penetration, according to an exemplary embodiment described and illustrated herein. In FIG. 15A, lancing device 100 or lancing device 150 has been loaded with new lancet L2, as illustrated in FIG. 14D. Lancet depth adjustment member and cap 200 is moved into lancing device distal end 110, in the direction indicated by arrow A16. In FIG. 15B, lancet depth adjustment member and cap 200 has been completely inserted into lancing device distal end 110, and grip 302 is moved into the locked position, as indicated by arrow A17. In FIG. 15C, the depth is set by rotating lancet depth adjustment member and cap 200, in the direction indicated by arrow A18, and observing depth indicators 216 in depth window 1205. As mentioned previously, depth indicators 216 correlate to specific depth stops 222, and establish the position at which stop tip 624 hits depth stops 222. The position at which stop tip 624 hits depth stops 222 establishes the travel of movable member 600 or 605, and therefore the depth of penetration of needle N into the target site. In FIG. 15B, there is a significant gap between stop 206 and outside edge 314 because lancing device 100 or lancing device 150 is at its rest position, and is not primed.

Figure 16A:
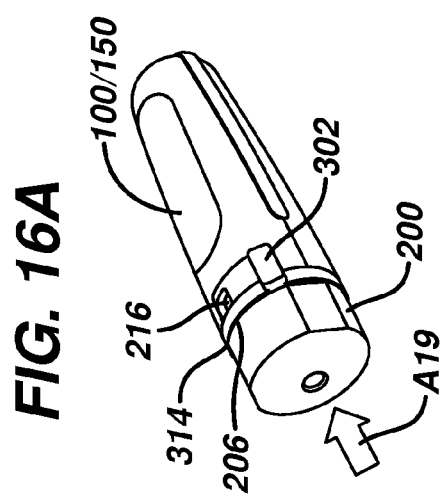
FIGS. 16A-16F illustrate a sequence of steps used in automatically firing a lancing device, according to an exemplary embodiment described and illustrated herein.
Figure 16B:
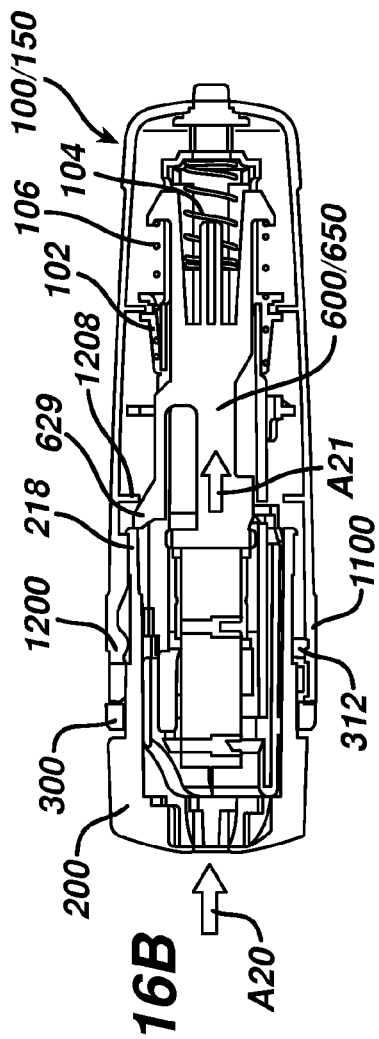
Figure 16C:
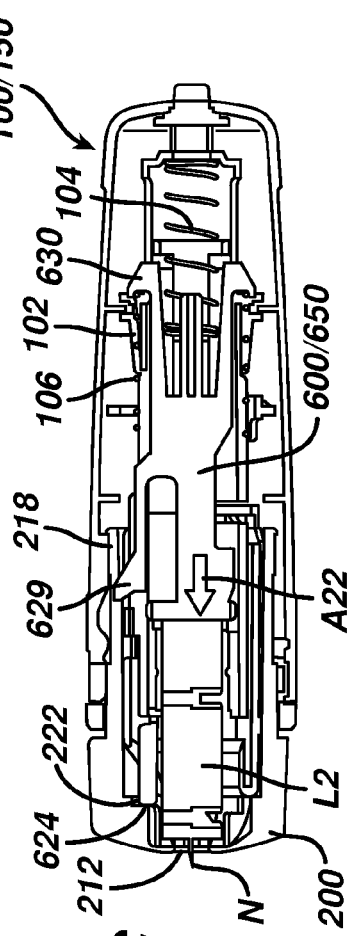
Figure 16D:
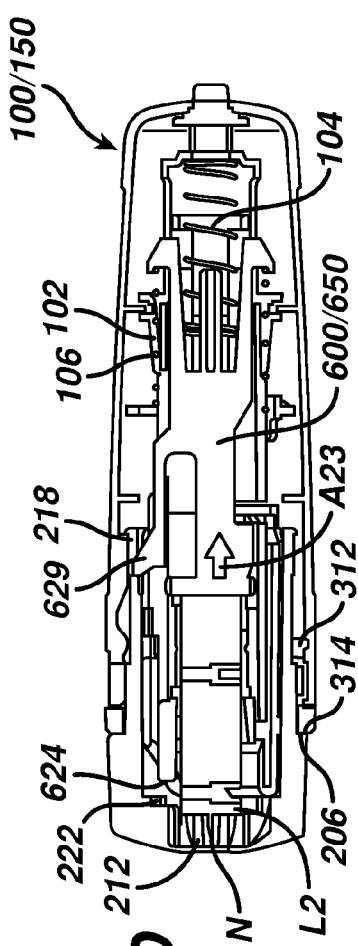

FIGS. 16A-16D illustrate a sequence of steps used in automatically firing lancing device 100 or lancing device 150, according to an exemplary embodiment described and illustrated herein. In FIG. 16A, lancet depth adjustment member and cap 200 makes contact with a target site (not shown for clarity) and is pushed in, as indicated by arrow A19. Stop 206 (FIG. 16D) moves toward outside edge 314, while grip 302 is in its locked position and depth indicators 216 indicate the depth of penetration. In FIG. 16B, lancet depth adjustment member and cap 200 has made initial contact with a target site, and is pushed in the direction indicated by arrow A20. Locking fingers 218 pushes on priming catch 629, moving movable member 600 or movable member 650 in the direction indicated by arrow A21. Priming catch 629 makes initial contact with firing ramp 1208, but has not yet been pushed inward and is still caught on the edge of locking fingers 218. While movable member 600 or movable member 650 move in the direction indicated by arrow A21, first bias member 104 compresses, building force used during the firing step. In FIG. 16C, priming catch 629 has been pushed in enough to clear locking fingers 218 and first bias member 104 pushes movable member 600 or movable member 650 in the direction indicated by arrow A22. At maximum travel in FIG. 16C, stop tip 624 strikes depth stops 222, while needle N travels through opening 212 and into the target site. While movable member 600 or movable member 650 travels in the direction indicated by arrow A22, first bias member 104 expands, and return arms 630 grab and expand second bias member 106. Once stop tip 624 hits depth stops 222, second bias member 106 pulls movable member 600 or movable member 650 back towards the home position, as indicated by arrow A23 in FIG. 16D. In FIG. 16D, needle N has moved back through opening 212, first bias member 104 and second bias member 106 have moved to a balanced position, and stop tip 624 is no longer in contact with depth stops 222.

Figure 16E:
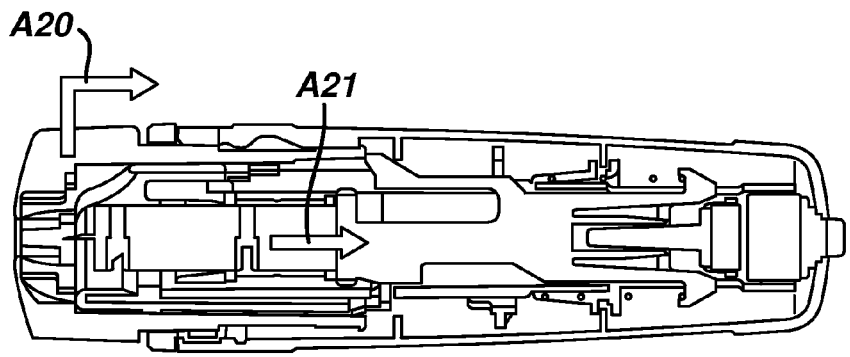
Figure 16F:
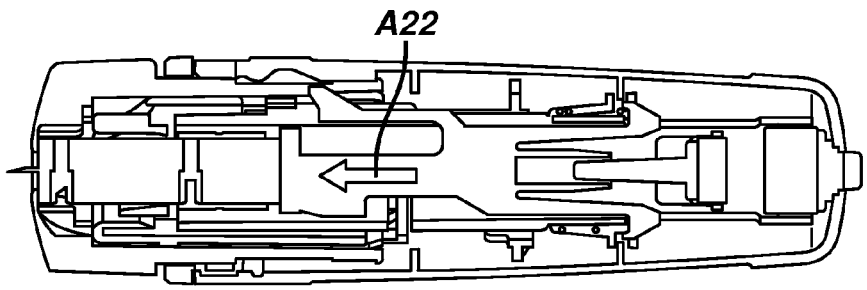
Figure 16G:
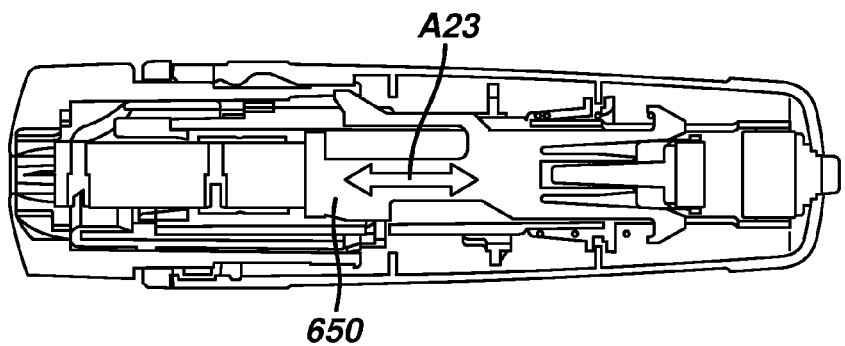
FIG. 16G illustrates an alternate main housing body.
Figure 16H:
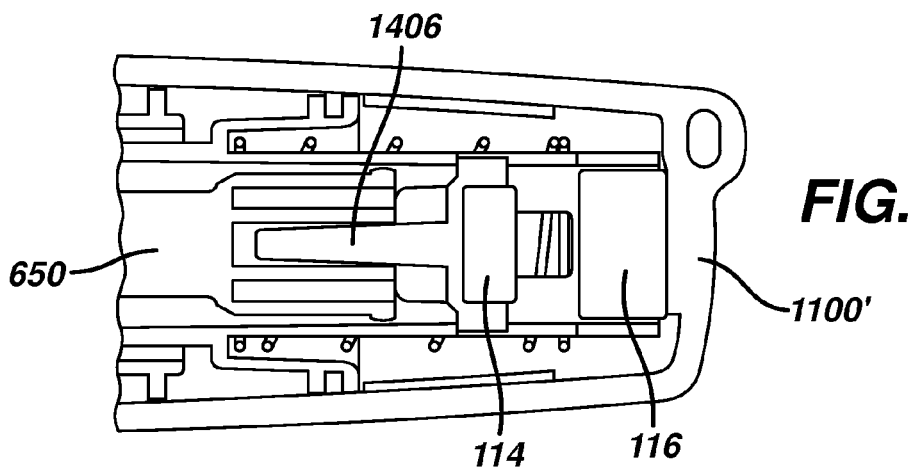
FIG. 16H illustrates an alternate main housing body.

FIGS. 16E-16G illustrate a similar sequence of priming and contemporaneously and automatically firing of the lancet N using a non-contact bias in the exemplary form of a magnet 116. For brevity, the operation of the embodiment shown in FIGS. 16E-16G is essentially identical to the operation in the embodiment shown in FIGS. 16A-16D.

FIGS. 17A-17B illustrate alternative first bias members in lancing device 100 or lancing device 150, according to embodiments described and illustrated herein. In FIG. 17A, first bias member 104 is a spring, and provides the force necessary for lancing. First bias member 104 is compressed when movable member 600 moves toward lancing device proximal end 108, and expands when movable member 600 moves toward lancing device distal end 110. In FIG. 17B, the first bias member includes floating magnet 114, fixed magnet 116, and floating magnet holder 1400. Floating magnet 114 and fixed magnet 116 are mounted with either their north or south poles facing each other, so as movable member 650, floating magnet holder 1400, and floating magnet 114 approach fixed magnet 116 during priming of lancing device 150, magnetic repulsion force is generated. Once lancing device 150 is fired, movable member 650, floating magnet holder 1400, and floating magnet 114 move away from fixed magnet 116, eventually reaching their maximum penetration depth. As lower finger 1414 and upper finger 1416 hit stops in second housing 750, floating magnet holder 1400 disengages from movable member 650, and movable member 650 travels toward lancing device distal end 110 using its forward momentum. Any type of permanent magnet can be used for floating magnet 114 and fixed magnet 116, such as, for example, neodymium-iron-boron (NIB) and other rare earth magnets.

Figure 18A:
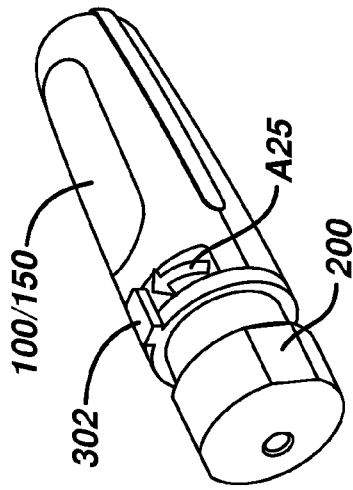
FIGS. 18A-18C illustrate a lancing device returning to home position and being unlocked, according to an exemplary embodiment described and illustrated herein.
Figure 18B:
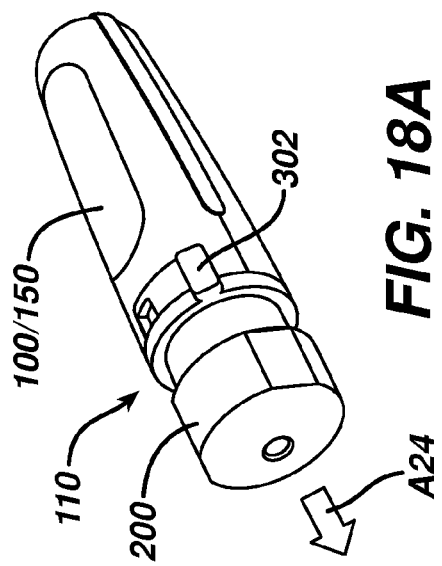
Figure 18C:
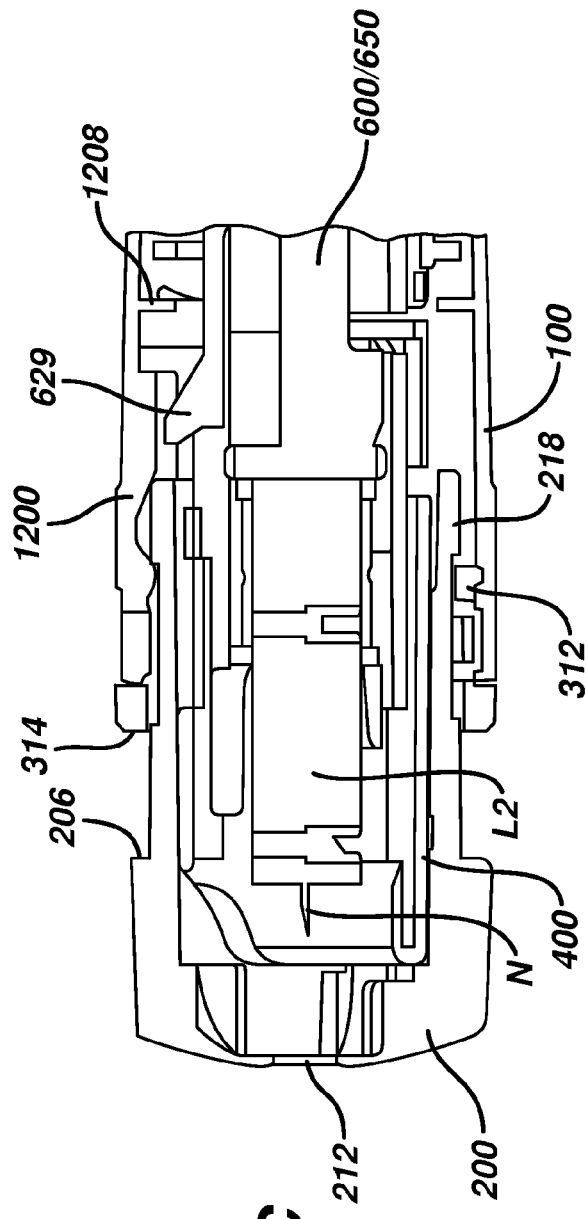

FIGS. 18A-18C illustrate lancing device 100 or lancing device 150 returning to home position and being unlocked, according to an exemplary embodiment described and illustrated herein. In FIG. 18A, an automatic prime and firing sequence has just been completed, as illustrated in FIG. 16D. Once lancet depth adjustment member and cap 200 is disengaged with the target surface, lancet depth adjustment member and cap 200 moves in the direction indicated by arrow A24. FIG. 18C is a cross sectional view of lancing device distal end 110 at the stage illustrated in FIG. 18A. In FIG. 18C, stop 206 has moved away from outside edge 314, locking fingers 218 have moved away from priming catch 629, and needle N has moved away from opening 212. In FIGS. 18A and 18C, lancing device 100 or lancing device 150 is in its home position. Grip 302 can be moved into an unlocked position, as indicated by arrow A25, preventing movable member 600 or movable member 650 from moving, and disabling the automatic prime and fire sequence. Although lancet depth adjustment member and cap 200 can be removed in this position, lancing device 100 or lancing device 150 cannot be accidentally primed or fired when grip 302 is in the unlocked position, illustrated in FIG. 18B.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A lancing device comprising:
   a housing having spaced apart proximal and distal ends disposed along a longitudinal axis;
   a movable member disposed in the housing and configured for movement along the longitudinal axis;
   a collar partially disposed in the housing and coupled to the movable member so that, during a lancing movement, the collar is movable concurrently and as a unit with the movable member at least in one direction along the longitudinal axis;
   a lancet coupled to the collar;
   a rotatable ring coupled to the collar; and
   a lancet depth adjustment member retained by both the rotatable ring and the collar so that the lancet depth adjustment member is rotatable relative to the housing to provide for a plurality of stop surfaces for the movable member as the movable member moves along the longitudinal axis to the distal end.

2. The lancing device of claim 1, further comprising:
   a chassis disposed in the housing, the chassis partially surrounding the movable member to provide a guide for movement of the movable member; and
   a first bias member located in the chassis to bias the movable member in a direction towards the distal end.

3. The lancing device of claim 2, in which the movable member includes a plurality of arms extending away from the longitudinal axis towards the distal end, one of the plurality of arms configured to engage a boss formed on an internal surface of the housing to retain the movable member against the first bias member in a primed position.

4. The lancing device of claim 1, in which the housing comprises two halves connected together.

5. The lancing device of claim 2, in which the chassis comprises a unitary member connected to a positioning band coupled to the housing, the chassis having at least one longitudinal groove that extends through the unitary member along the longitudinal axis to allow communication from the inside of the chassis to the inside of the housing.

6. The lancing device of claim 2, further comprising a second bias member configured to bias the movable member in a direction towards the proximal end.

7. The lancing device of claim 6, in which the movable member comprises at least one return arm that extends through the longitudinal groove so that the movable member is guided by the at least one return arm along a path defined by the longitudinal groove.

8. The lancing device of claim 7, in which the second bias member comprises a helical spring disposed outside the chassis and connected to the at least one return arm.

9. The lancing device of claim 4, in which the first bias member is selected from a group consisting of springs, magnets, or combinations thereof.

10. The lancing device of claim 7, further comprising a third bias member disposed in the housing to bias against the collar toward the distal direction along the longitudinal axis.

11. A lancing device comprising:
    a first housing having spaced apart proximal and distal ends disposed along a longitudinal axis;
    a second housing disposed in the first housing in a non-movable relationship with the first housing;
    a movable member disposed in the second housing and configured for movement along the longitudinal axis;
    a bias member located in the second housing to bias the movable member in a direction towards the distal end;
    a lancet coupled to the movable member so that the lancet moves as a unit with the movable member along the longitudinal axis;
    a depth adjustment member having a plurality of stop surfaces disposed radially about the longitudinal axis; and
    a rotatable lock ring engaging an inner surface of the first housing and an inner surface of the depth adjustment member to retain the depth adjustment member to the first housing in one radial position of the rotatable lock ring and to allow release of the depth adjustment member in another radial position of the rotatable lock ring relative to the longitudinal axis.

12. The lancing device of claim 11, in which the depth adjustment member includes at least one locking finger extending generally along the longitudinal axis.

13. The lancing device of claim 11, in which the movable member includes at least one actuation arm that extends generally along the longitudinal axis and configured to engage a boss formed on an internal surface of the first housing to retain the movable member against a first bias member in a primed position.

14. The lancing device of claim 11, further comprising a cylindrical collar disposed partially in the first housing and configured to surround a portion of the lancet, the cylindrical collar being in engagement with the movable member.

15. The lancing device of claim 11, in which the first housing comprises two halves connected together.

16. The lancing device of claim 11, in which the second housing comprises a unitary member connected to a positioning band coupled to the first housing, the second housing having at least one longitudinal groove that extends through the unitary member along the longitudinal axis to allow communication from the inside of the second housing to the inside of the first housing.

17. The lancing device of claim 11, further comprising a second bias member configured to bias the movable member in a direction towards the proximal end.

18. The lancing device of claim 16, in which the movable member comprises at least one return arm that extends through the longitudinal groove so that the movable member is guided by the at least one return arm along a path defined by the longitudinal groove.

19. The lancing device of claim 17, in which the second bias member comprises a helical spring disposed outside the second housing and connected to the at least one return arm.

20. The lancing device of claim 13, in which the first bias member is selected from a group consisting of springs, magnets, or combinations thereof.

21. A lancing device comprising:
a housing having spaced apart proximal and distal ends disposed along a longitudinal axis, the housing being devoid of any actuator or button on its outer surface;
a movable member disposed in the housing and configured for movement along the longitudinal axis;
a lancet inserted into the movable member; and
a cap enclosing the lancet, the cap having a plurality of fingers that extend along the longitudinal axis to engage the moveable member and move the movable member towards the proximal end against a bias force such that at a predetermined position along the longitudinal axis, the plurality of fingers disengage from the movable member to allow the movable member to move in an opposite direction toward the distal end, thereby allowing the lancet to extend through the cap.

* * * * *